(12) United States Patent
Liu et al.

(10) Patent No.: US 12,303,224 B2
(45) Date of Patent: May 20, 2025

(54) SURGICAL ROBOT

(71) Applicants: GAMANIA DIGITAL ENTERTAINMENT CO., LTD, Taipei (TW); CATHAY GENERAL HOSPITAL, Taipei (TW)

(72) Inventors: Po-Yun Liu, Taipei (TW); Chun-Hung Kuo, Taipei (TW); Chih-Cheng Chien, Taipei (TW); Yen-Chieh Wang, Taipei (TW)

(73) Assignees: Gamania Digital Entertainment Co., Ltd., Taipei (TW); Cathay General Hospital, Taipei (TW)

( * ) Notice: Subject to any disclaimer, the term of this patent is extended or adjusted under 35 U.S.C. 154(b) by 471 days.

(21) Appl. No.: 17/944,466

(22) Filed: Sep. 14, 2022

(65) Prior Publication Data

US 2024/0074826 A1    Mar. 7, 2024

(30) Foreign Application Priority Data

Sep. 1, 2022 (TW) .................................. 111133234

(51) Int. Cl.
*A61B 34/37* (2016.01)
*A61B 34/00* (2016.01)
*A61B 34/30* (2016.01)
*A61B 90/00* (2016.01)

(52) U.S. Cl.
CPC .............. *A61B 34/37* (2016.02); *A61B 34/76* (2016.02); *A61B 2034/305* (2016.02); *A61B 2090/064* (2016.02)

(58) Field of Classification Search
CPC ... A61B 34/37; A61B 34/76; A61B 2034/305; A61B 2090/064; A61B 34/71; A61B 2034/715
See application file for complete search history.

(56) References Cited

U.S. PATENT DOCUMENTS

2009/0088775 A1*  4/2009  Swarup ................. A61B 34/71
                                                                   700/264

* cited by examiner

*Primary Examiner* — Tan-Uyen T Ho
*Assistant Examiner* — Khoa Tan Le
(74) *Attorney, Agent, or Firm* — Rosenberg, Klein & Lee

(57) ABSTRACT

A surgical robot including at least one contact module, a control connection module, at least one first robotic arm, and at least one grip control device. A first transmission member of the control connection module drives the control module through a first transmission connecting member. A first shaft member of the first robotic arm is connected with the first transmission member while the grip control device is connected with the first robotic arm by a transmission interface. A force sensing member of the first robotic arm detects a first reaction force from the contact module so that the first robotic arm sends a feedback control signal to the grip control device to control a grip driving member to generate a force feedback for allowing a grip portion to move. Thereby, users can feel movement of the grip portion caused by the force feedback to avoid accidental iatrogenic injuries.

10 Claims, 25 Drawing Sheets

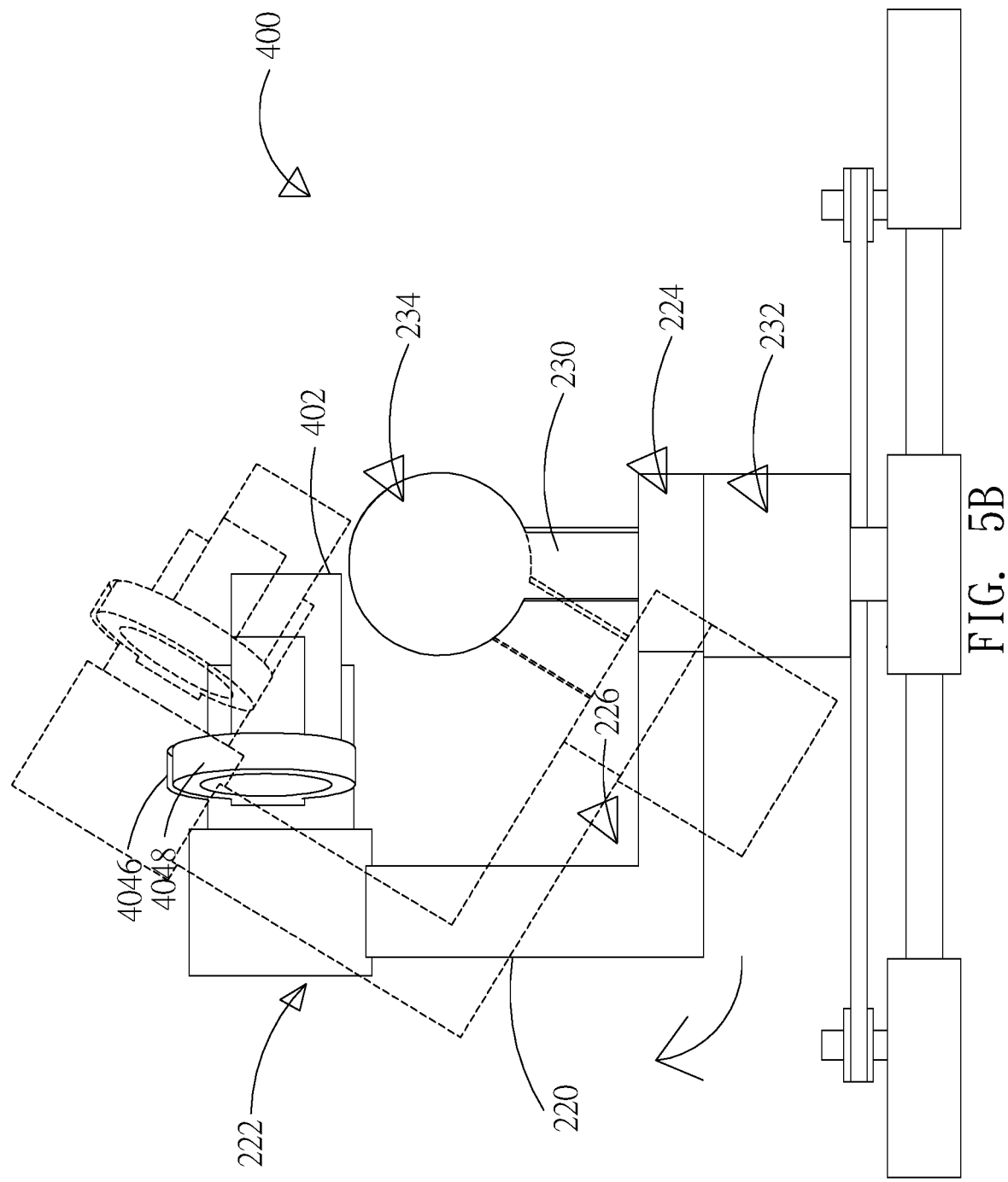

SURGICAL ROBOT

FIELD OF THE INVENTION

The present invention relates to a robot, especially to a surgical robot.

BACKGROUND OF THE INVENTION

Along with prosperous development of mechanics, automatic control and computing technology, robotic arms provide highly-efficient and stable automated control, especially while being applied to remote operation.

Generally, surgical robots are robots performing minimally invasive surgery under control of a console operated by surgeons such as Da Vinci Surgical System. The surgical robot carries out surgical procedure by robotic arms.

Although the surgical robot performs minimally invasive and stable surgery by semi-automatic control, surgeons or operators who control the robotic arms are unable to learn the control state of the surgical instruments easily, like using handheld instruments in contact with organs and tissues for repair or removal of the organs and tissues. The operator of the surgical robot uses a remote console for control of the surgical robot to carry out the operation at the remote end so that he is unable to learn the force acted on the robotic arm of the surgical robot at the moment and accidents may occur during the operation. Moreover, the operators are unable to make a response in a real-time manner and this comes with certain risks.

In order to avoid the accidents occurred under the condition that the force applied to the robotic arm is unable to be learned during the remote operation, there is an urgent need to make the robotic arm of the surgical robot get the force applied to the surgical instruments as well as operators of the surgical robot learn the force acted on the surgical instruments in a real time manner.

Thus there is room for improvement and there is a need to provide a novel surgical robot which includes a first force sensing member on a first robotic arm to detect a first reaction force from a contact module and generate a first sensing signal. Then the sensing signal is sent to a first communication control circuit and transferred to a second communication control circuit of a grip control device so that the second communication control circuit generates and sends a feedback control signal to a grip driving member for control of the grip driving member to generate a force feedback for allowing a grip portion to move.

SUMMARY OF THE INVENTION

A primary objective of the present invention is to provide a surgical robot in which a first force sensing member on a first robotic arm detects a contact module which is connected with a control connection module through a first transmission member and a first transmission connecting member. Thereby a first reaction force is transferred from the contact module to the first force sensing member correspondingly and a first sensing signal is generated and sent to the first communication control circuit. Then the sensing signal is transferred to a second communication control circuit of a grip control device and the second communication control circuit generates a corresponding feedback control signal sent to a grip driving member for control of the grip driving member. Thu the grip driving member generates a force feedback for allowing a grip portion to move. Thereby users can learn the control state of the contact module by the grip driving member linked to the grip portion, not only to avoid accidental iatrogenic injuries caused by too much force applied, but also to perform the surgical procedure more precisely.

In order achieve the above objects, a surgical robot according to the present invention includes at least one contact module, a control connection module, at least one first robotic arm, and at least one grip control device. The control connection module is provided with a first main body and a rod. A first end of the rod is inserted through the first main body. A first transmission member is mounted in the control connection module and used for driving a first end of a first transmission connecting member while a second end of the first transmission connecting member is inserted through the rod and connected with the contact module at a second end of the rod. The first robotic arm consists of a first shaft member, a first communication control circuit, and a first force sensing member electrically connected with the first communication control circuit and linked to the first shaft member. A first reaction force is transferred from the contact module to the first force sensing member through the first transmission connecting member, the first transmission member, and the first shaft member. The first force sensing member detects the first reaction force and generates a first sensing signal which is sent to a second communication control circuit of the grip control device. Thus the second communication control circuit generates a feedback control signal according to the first sensing signal and the feedback control signal is sent to a grip driving member. Then the grip driving member is controlled to generate a force feedback for allowing the grip portion to move. Therefore, the users can learn the control state of the contact module by the grip driving member linked to the grip portion so that not only iatrogenic injuries caused by excessive force applied can be avoided, the surgical procedure can also be performed more precisely.

Preferably, the contact module is provided with a first contact member and a second contact member. The first reaction force and a second reaction force are respectively corresponding to the first contact member and the second contact member. The second end of the first transmission connecting member is inserted through the rod and connected with the first contact member at the second end of the rod. The first reaction force is transferred from the first contact member to the first force sensing member through the first transmission connecting member, the first transmission member, and the first shaft member. A second transmission member and a second transmission connecting member are mounted in the first main body. The second transmission member drives a first end of the second transmission connecting member to move while a second end of the transmission connecting member is inserted through the rod and connected with the second contact member at the second end of the rod. The first robotic arm further includes a second shaft member and a second force sensing member which are respectively linked to the second transmission member and the second shaft member. The second force sensing member is electrically connected with the first communication control circuit and used for detecting a second reaction force. The second reaction force is transferred from the second contact member to the second force sensing member through the second transmission connecting member, the second transmission member, and the second shaft member and thus a second sensing signal is generated. The first force sensing member and the second force sensing member respectively send the first sensing signal and the sensing signal to the first communication control circuit. Then the first communication control circuit sends the first and the second sensing signals to the second communication control circuit through a remote transmission interface so that the second communication control circuit generates a corresponding feedback control signal which is sent to the grip driving member for control of the grip driving member. Thereby the grip driving member generates the force feedback for driving the grip portion to move.

Preferably, the control connection module consists of the first main body, the rod, the first transmission member, the first transmission connecting member, the second transmission member, the second transmission connecting member, a third transmission member, a third transmission connecting member, a fourth transmission member, and a fourth transmission connecting member. The first main body is composed of a cover body, a bottom plate, and a fixing base. The first transmission member, the second transmission member, the third transmission member, the fourth transmission member, and the fixing base are all disposed on the bottom plate. A first end of the rod is pivotally connected with the fixing base and inserted through the cover body while a second end of the rod is provided with a contact module. The first transmission member, the second transmission member, the third transmission member, and the fourth transmission member are arranged adjacent to one another. One end of the first transmission connecting member is wound around the first transmission member while the other end of the first transmission connecting member is inserted through the rod and wound around the first contact member of the contact module. The first transmission member drives the first contact member to move through the first transmission connecting member so that the first contact member swings relative to the rod with a first degree of freedom.

One end of the second transmission connecting member is wound around the second transmission member while the other end of the second transmission connecting member is inserted through the rod and wound around the second contact member of the contact module. The second transmission member drives the second contact member to move through the first transmission connecting member so that the second contact member swings relative to the rod with the first degree of freedom. One end of the third transmission connecting member is wound around the third transmission member and the other end thereof is inserted through the rod and wound around the contact module. While the third transmission member is rotating, the contact module is driven through the third transmission connecting member. Thus the contact module swings relative to the rod with a second degree of freedom in a second axial direction. Two ends of the fourth transmission connecting member are wound around the fourth transmission member and the first end of the rod correspondingly. During rotation of the fourth transmission member, the rod is adjusted through the fourth transmission connecting member so that the rod is rotated around its central axis.

Preferably, the control connection module further includes a first pulley and a second pulley respectively arranged between the first and the fourth transmission members and between the second and the third transmission members. The first pulley is used to help the first transmission connecting member enter the rod smoothly while the second pulley is used to help the second and the third transmission connecting members enter the rod smoothly.

Preferably, the first robotic arm further incudes a first drive module, a second drive module, a third shaft member, a third drive module, a fourth shaft member, and a fourth drive module. The first drive module, the second drive module, the third drive module, and the fourth drive module are all electrically connected with the first communication control circuit. The first drive module is disposed on one side of the first force sensing member and the first shaft member while the second drive module is arranged at one side of the second force sensing member and the second shaft member. The third drive module and the fourth drive module are arranged adjacent to each other, disposed adjacent to the first and the second shaft members, and respectively connected with the third shaft member and the fourth shaft member for driving the third shaft member and the fourth shaft member correspondingly. The second communication control circuit generates and sends a drive control signal to the first communication control circuit so that the first communication control circuit generates and sends a drive signal to the first, the second, the third and the fourth drive modules according to the drive control signal for control of the first, the second, the third and the fourth drive modules to drive the first, the second, the third, and the fourth shaft members correspondingly.

Preferably, the first drive module, the second drive module, the third drive module, and the fourth drive module can be a swing motor driver or an integrated motor driver while the first force sensing member and the second force sensing member are load cells.

Preferably, the first robotic arm further includes a fifth shaft member, a fifth drive module, a third force sensing member, a fourth force sensing member, and a fifth force sensing member. The third force sensing member is electrically connected with the first communication control circuit and linked to the third shaft member for detecting a third reaction force and generating a third sensing signal. The third reaction force is transferred from the contact module to the third force sensing member through the third transmission connecting member, the third transmission member, and the third shaft member. The fourth force sensing member is electrically connected with the first communication control circuit and linked to the fourth shaft member for detecting a fourth reaction force and generating a fourth sensing signal. The fourth reaction force is transferred from the rod to the fourth force sensing member through the fourth transmission connecting member, the fourth transmission member, and the fourth shaft member. The fifth drive module and the fifth shaft member are disposed on one side of the first robotic arm while the fifth drive module is electrically connected with the first communication control circuit. The fifth force sensing member is arranged at one side of the fifth drive module and connected with the first main body of the first robotic arm. The fifth drive module drives the fifth force sensing member and the fifth shaft member to move. The first communication control circuit generates and sends a drive signal to the fifth drive module for control of the fifth drive module to move the fifth force sensing member by pulling or pushing. Thereby the first main body is driven to have a displacement. The fifth force sensing member detects deformation of the fifth force sensing member itself and generates a fifth reaction force and then generates and sends a fifth sensing signal to the first communication control circuit. The first communication control circuit further sends the fifth sensing signal to the second communication control circuit.

Preferably, the fifth drive module can be a swing motor driver or an integrated motor driver while the third force sensing member is a load cell.

Preferably, the grip control device includes a plurality of cantilevers, a plurality of cantilever drivers, a control base, and at least one displacement driving module. The cantilevers are connected to one another end-to-end and also connected with the grip driving member while the cantilever drivers pivotally connected with connection areas of the cantilevers and linked to the cantilevers. The control base is connected to a rear end of the connected cantilevers and provided with the second communication control circuit which is electrically connected with the grip driving member and the cantilever drivers. The second communication control circuit receives the first sensing signal and the second sensing signal through the remote transmission interface and hence generates the feedback control signal for control of the grip driving member and the cantilever drivers to generate the force feedback. Thus both the grip portion and cantilevers are driven to move. Moreover, the displacement driving module is disposed on one side of the control base, electrically connected with the second communication control circuit, and linked to the control base for control of displacement of the control base. The second communication control circuit further produces a corresponding feedback control signal according to force feedback information for driving the displacement driving module to make the control base move.

Preferably, the grip driving member, the cantilever drivers, and the displacement driving module can be a swing motor driver or an integrated motor driver.

Preferably, the grip control device includes a plurality of cantilevers, a plurality of cantilever drivers, and a control base. The cantilevers are connected end-to-end and also connected with the grip driving member while the cantilever drivers pivotally connected with connection areas of the cantilevers and linked to the cantilevers. The control base is connected to a rear end of the connected cantilevers and provided with the second communication control circuit which is electrically connected with the grip driving member and the cantilever drivers. The second communication control circuit receives the first sensing signal and the second sensing signal through the remote transmission interface and hence generates the feedback control signal for control of the grip driving member and the cantilever drivers to generate the force feedback. Thus both the grip portion and cantilevers are driven to move.

Preferably, the grip driving member and the cantilever drivers can be a swing motor driver or an integrated motor driver.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 5B is a schematic drawings showing a grip control device swinging vertically of an embodiment according to the present invention;

DETAILED DESCRIPTION OF THE PREFERRED EMBODIMENT

In order to learn technical content, purposes and functions of the present invention more clearly and completely, please refer to the following detailed descriptions with the figures and reference signs.

While using conventional surgical robots for operations, operators are unable to learn the state of surgical instruments like normal operations in which the surgical instruments are manually operated and in contact with organs or tissues going to be removed or repaired. While operators of the surgical robots operate robotic arms at the remote end, they don't know force conditions of the robotic arms at the moment. Once accidents occur, the operators can't respond immediately and this comes with certain risks including injuries. Compared with the conventional surgical robot, the present surgical robot not only avoids accidental iatrogenic injuries caused by too much force applied, but also performs the surgical procedure more precisely.

Moreover, surgical instruments on the robotic arm used during minimally invasive surgery or remote operations is usually provided with a sensor arranged at a front end of the surgical instrument and fixed on one side of the surgical instrument by silicone or other medical grade adhesives. However, the surgical instrument may be used in an environment containing acid or alkaline substance. Thus the sensor may be damaged and thus need to be replaced. This is not only lead to the increasing cost, but also increasing surgical risk such as falling of the sensor from the surgical instrument to be left in patient's body.

The surgical robot of the present invention features on that the surgical robot uses a force sensing member disposed on one side of a shaft member not only to detect a reaction force sent back by surgical instruments on a control connection module of a first robotic arm, but also to feed back forces applied during the operation through the reaction force captured by the force sensing member. Thereby surgical risk caused by excessive force applied can be avoided.

The followings are detailed descriptions of a plurality of embodiments of the present invention with reference to figures. These embodiments are not intended to limit the scope of the invention.

Figure 1:
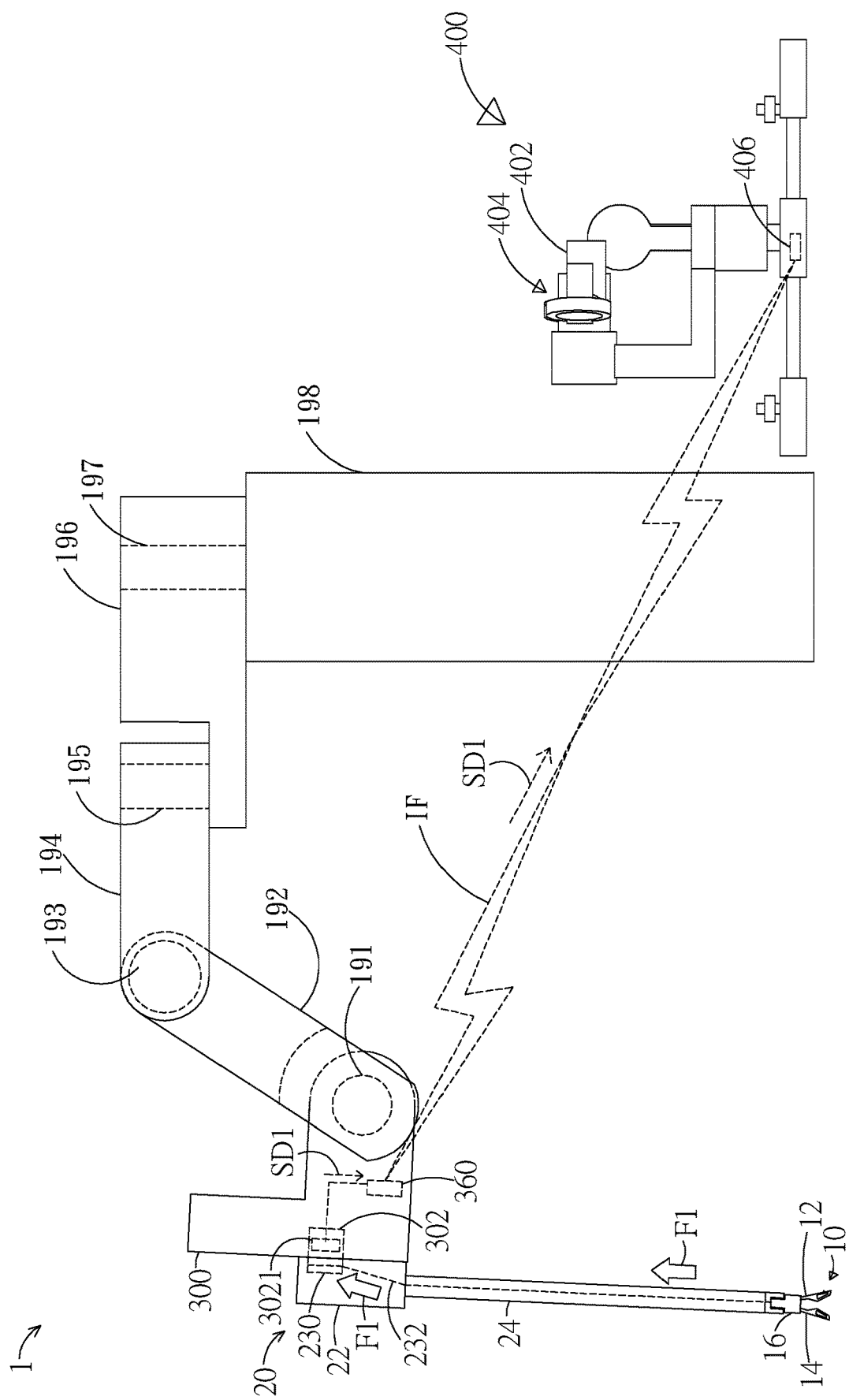
FIG. 1 is a schematic drawing showing structure of a surgical robot of an embodiment according to the present invention.

Refer to FIG. 1, an embodiment of a surgical robot is revealed. A shown in the figure, a surgical robot 1 according to the present invention includes at least one contact module 10, a control connection module 20, at least one first robotic arm 300, and at least one grip control device 400. The control connection module 20 is disposed on one end of the first robotic arm 300 and provided with a first main body 22 and a rod 24. A first end and a second end of the rod 24 are respectively inserted through the first main body 22 and connected to the contact module 10. A first transmission member 230 is mounted in the control connection module 20 and connected to a first end of a first transmission connecting member 232 while the contact module 10 is arranged at a second end of the first transmission connecting member 232. The first robotic arm 300 consists of a first shaft member (axial member) 302 linked to the first transmission member 230, a first force sensing member 3021 disposed on one side of the first shaft member 302 and linked to the first shaft member 302, and a first communication control circuit 360. The first force sensing member 3021 is linked to the first shaft member 302 through a first power transmission member 3022 and used to detect a first reaction force F1 and generate a first sensing signal SD1 which is sent to the first communication control circuit 360. The first reaction force F1 is transferred from the contact module 10 to the first force sensing member 3021 through the first transmission connecting member 232, the first transmission member 230, and the first shaft member 302. The first force sensing member 3021 sends the first sensing signal SD1 to the first communication control circuit 360. The first reaction force F1 becomes a pull force, tensile force, thrust force, or pressure acted on the first force sensing member 3021 so that the first force sensing member 3021 generates a voltage signal or a current signal used as the first sensing signal SD1.

The grip control device 400 consists of a grip driving member 402, a grip portion 404, and a second communication control circuit 406. The grip driving member 402 is linked to the grip portion 404 and electrically connected with the second communication control circuit 406. The second communication control circuit 406 is connected with the first communication control circuit 360 through a remote transmission interface IF and also receiving the first sensing signal SD1 through the remote transmission interface IF to generate a corresponding feedback control signal FBC for control of the grip driving member 402. Thereby the grip driving member 402 generates a force feedback for driving the grip portion 404 to move. That means the second communication control circuit 406 generates the feedback control signal FBC according to the first sensing signal SD1 and the feedback control signal FBC is sent to the grip driving member 402. Then the grip driving member 402 generates the force feedback according to the feedback control signal FBC for allowing the grip portion 404 to move.

Figure 2A:
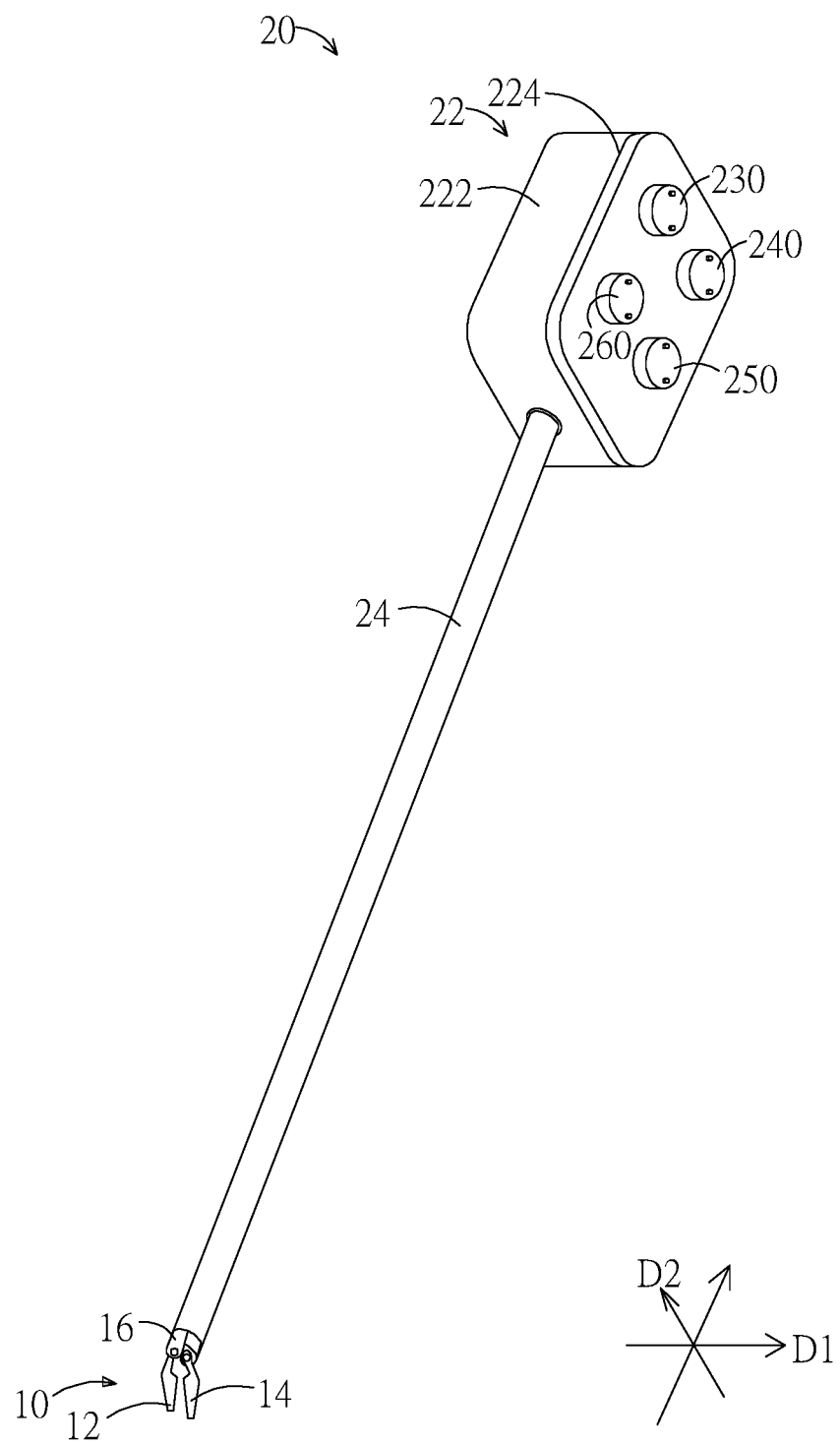
FIG. 2A is a perspective view of a control connection module of an embodiment according to the present invention.
Figure 2B:
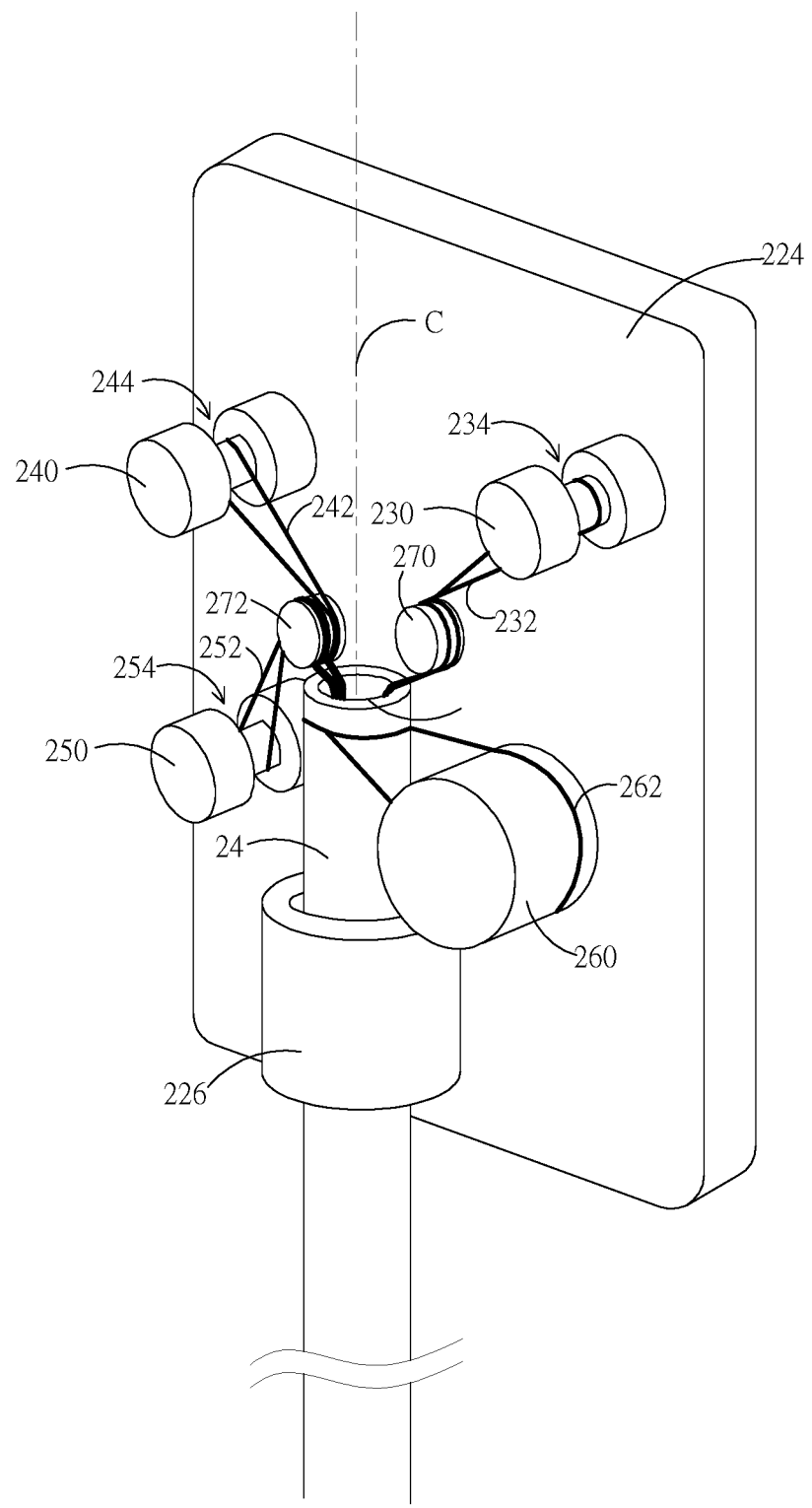
FIG. 2B is a schematic drawing showing inner structure of a control connection module of an embodiment according to the present invention.

Refer to FIG. 2A and FIG. 2B, the control connection module 20 of an embodiment is revealed. As shown in figures, the control connection module 20 is composed of the first main body 22 and the rod 24. The first main body 22 is provided with a cover body 222 and a bottom plate 224. One end of the rod 24 is inserted through the cover body 222 while the other end of the rod 24 is extended to the contact module 10 and connected with the contact module 10 by a reel member 16. The contact module 10 and the reel member 16 can be integrated into one part.

The first transmission member 230, the first transmission connecting member 232, a second transmission member 240, a second transmission connecting member 242, a third transmission member 250, a third transmission connecting member 252, a fourth transmission member 260, and a fourth transmission connecting member 262 are all arranged at the bottom plate 224. In the control connection module 20, a fixing base 226 is disposed on the bottom plate 224 while a first end of the rod 24 is inserted through the cover body 222 to be pivotally arranged at the fixing base 226 and a second end of the rod 24 is provided with the reel member 16.

In this embodiment, the first transmission member 230, the second transmission member 240, the third transmission member 250, and the fourth transmission member 260 of the control connection module 20 are disposed on the bottom plate 224 adjacent to one another and covered by the cover body 222. One end of the first transmission connecting member 232 is wound and mounted in a first groove 234 of the first transmission member 230 while the other end of the first transmission connecting member 232 is wound around a first pulley 270 and then inserted in and extended along the rod 24 to be wound around the contact module 10. One end of the second transmission connecting member 242 is wound and mounted in a second groove 244 of the second transmission member 240 while the other end of the second transmission connecting member 242 is wound around a second pulley 272 and then inserted in and extended along the rod 24 to be wound around the contact module 10. As to the third transmission connecting member 252, one end is wound and mounted in a third groove 254 of the third transmission member 250 while the other end thereof is wound around the second pulley 272 and then inserted in and extended along the rod 24 to be wound around the reel member 16. The first pulley 270 is used to help the first transmission connecting member 232 enter the rod 24 smoothly while the second pulley 272 is used to help the second and the third transmission connecting members 242, 252 enter the rod 24 smoothly.

Two ends of the fourth transmission connecting member 262 are wound around the fourth transmission member 260 and the first end of the rod 24 correspondingly. During rotation of the fourth transmission member 260, the rod 24 is adjusted through the fourth transmission connecting member 262 and rotated around a central axis C of the rod 24. The rod 24 is provided with a hollow portion 248 through which the first transmission connecting member 232, the second transmission connecting member 242, and the third transmission connecting member 252 are inserted and extended to connect with the contact module 10 and the reel member 16. The contact module 10 is provided with a first contact member 12 and a second contact member 14. During rotation, the first transmission member 230 drives the first contact member 12 of the contact module 10 through the first transmission connecting member 232. Similarly, during rotation, the second transmission member 240 drives the second contact member 14 of the contact module 10 through the second transmission connecting member 242. Thus the first and the second contact members 12, 14 of the contact module 10 swing relative to the reel member 16 with a first degree of freedom in a first axial direction D1. While rotating, the third transmission member 250 drives the reel member 16 through the third transmission connecting member 252 so that the reel member 16 swings relative to the rod 24 with a second degree of freedom in a second axial direction D2. The present is not limited to the above embodiment. When the contact module 10 includes only a single contact member, the control connection module 20 only needs to be provided with the first transmission member 230 and the first transmission connecting member 232 for driving the contact module 10 to move, without arrangement of the second transmission member 240 and the second transmission connecting member 242.

Moreover, the contact module 10 can be a holding device, a drill, a file, a scraper, a saw, a screwdriver, or a surgical instrument which repairs or removes a part of tissues by drilling, polishing, cutting, or scraping.

Figure 2C:
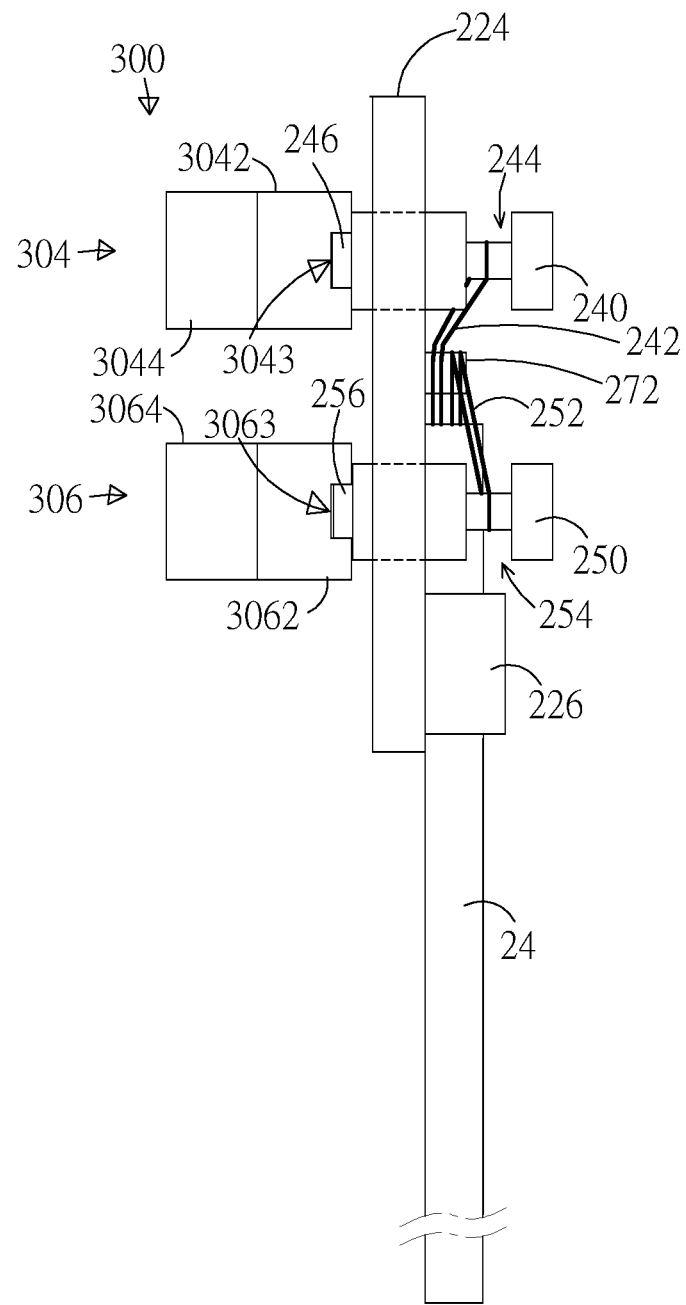
FIG. 2C is a left side view of a control connection module of an embodiment connected with a part of a first robotic arm according to the present invention.
Figure 2D:
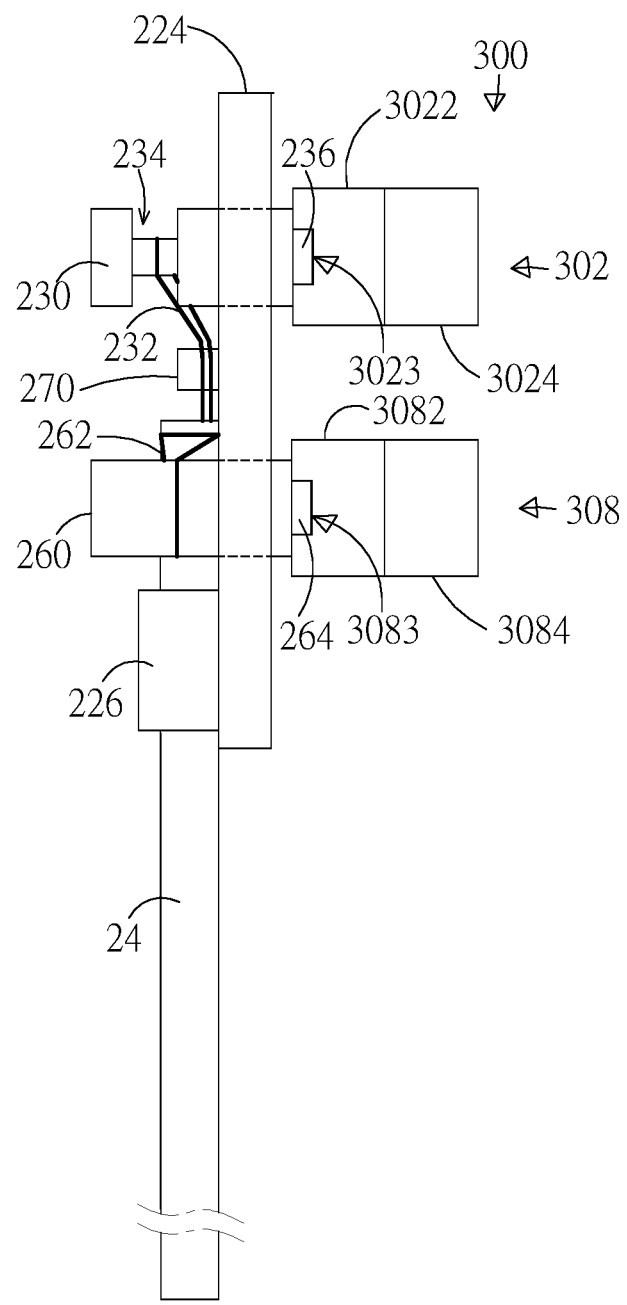
FIG. 2D is a right side view of a control connection module of an embodiment connected with a part of a first robotic arm according to the present invention.

Refer to FIG. 2C and FIG. 2D, two side views of a control connection module of an embodiment connected with a part of a first robotic arm according to the present invention are revealed. As shown in the figures, the control connection module 20 is disposed on one end of a first robotic arm 300 which is provided with a first shaft member 302, a second shaft member 304, a third shaft member 306, and a fourth shaft member 308 which are respectively connected with the first transmission member 230, the second transmission member 240, the third transmission member 250, and the fourth transmission member 260 for driving the first transmission member 230, the second transmission member 240, the third transmission member 250, and the fourth transmission member 260 to rotate correspondingly. Through rotation of the above first shaft member 302, the second shaft member 304, the third shaft member 306, and the fourth shaft member 308, the rod 24 and the contact module 10 are driven to have further action. The first shaft member 302, the second shaft member 304, the third shaft member 306, and the fourth shaft member 308 are respectively provided with a first upper transmission member 3022, a second upper transmission member 3042, a third upper transmission member 3062, and a fourth upper transmission member 3082 which are respectively joined with a first connecting member 236 of the first transmission member 230, a second connecting member 246 of the second transmission member 240, a third connecting member 256 of the third transmission member 250, and a fourth connecting member 266 of the fourth transmission member 260 through a first depression 3023, a second depression 3043, a third depression 3063, and a fourth depression 3083.

Refer to FIG. 2A, FIG. 2E-2H, FIG. 3 and FIG. 6, structure of a part of the first robotic arm, sensing of reaction force and signal transmission, and swing of the contact module in a first axis are disclosed. As shown in FIG. 2C, FIG. 2D, and FIG. 6A, the contact module 10 which is composed of the first contact member 12 and the second contact member 14 is further provided with the reel member 16 in which a first reel part 122 and a second reel part 142 are pivotally disposed. The first reel part 122 and the second reel part 142 are respectively linked to the first contact member 12 and the second contact member 14. Thereby the first transmission member 230 is further connected with the first reel part 122 through the first transmission connecting member 232. Thus the first shaft member 302 which is connected with the first transmission member 230 is linked to the first contact member 12 through the first transmission connecting member 232. Similarly, the second transmission member 240 is further connected with the second reel part 142 through the first transmission connecting member 242 so that the second shaft member 304 which is connected with the second transmission member 240 is linked to the second contact member 14 through the second transmission connecting member 242.

Figure 2E:
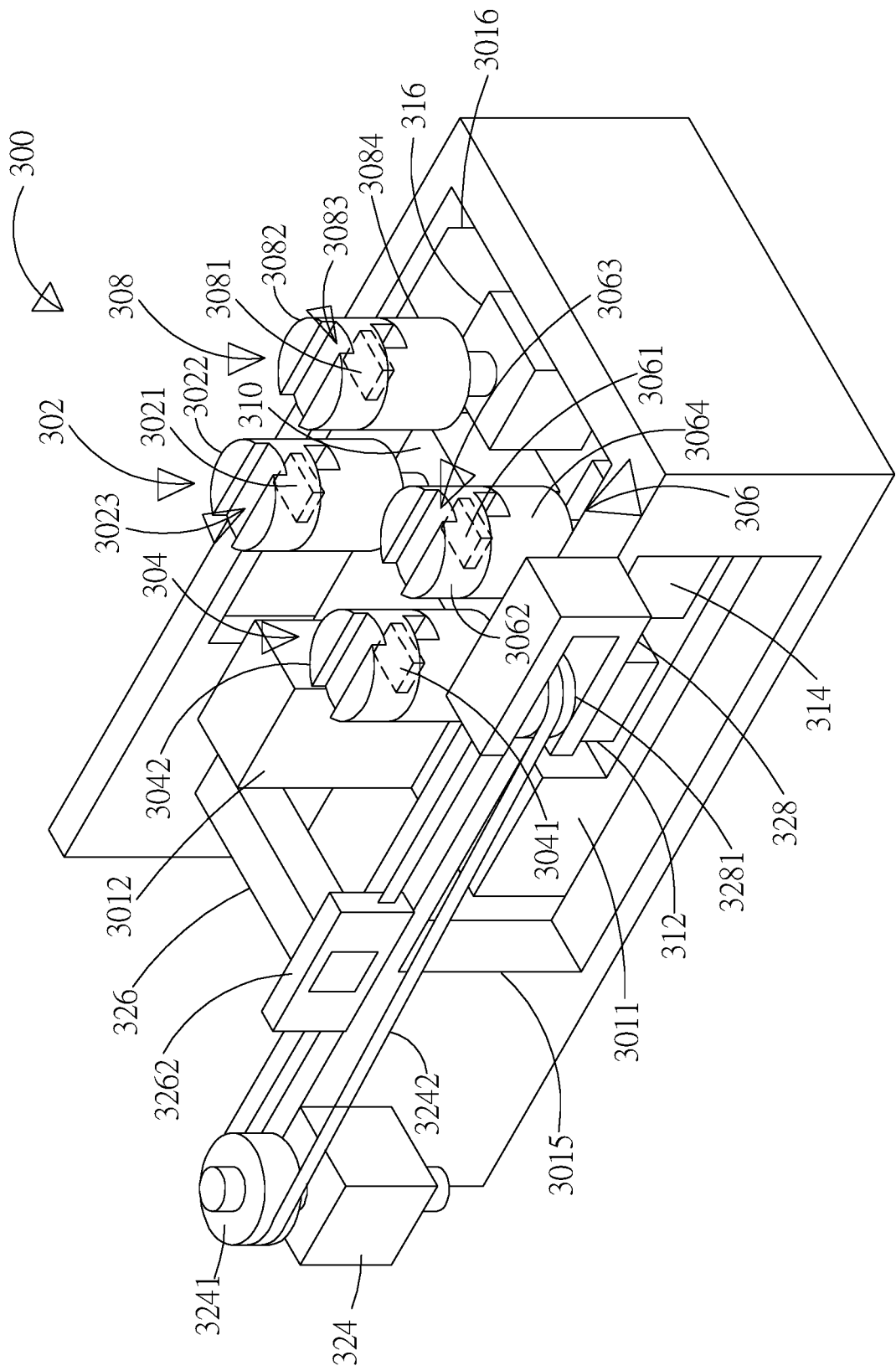
FIG. 2E is a schematic drawing showing structure of a part of a first robotic arm of an embodiment according to the present invention.
Figure 2F:
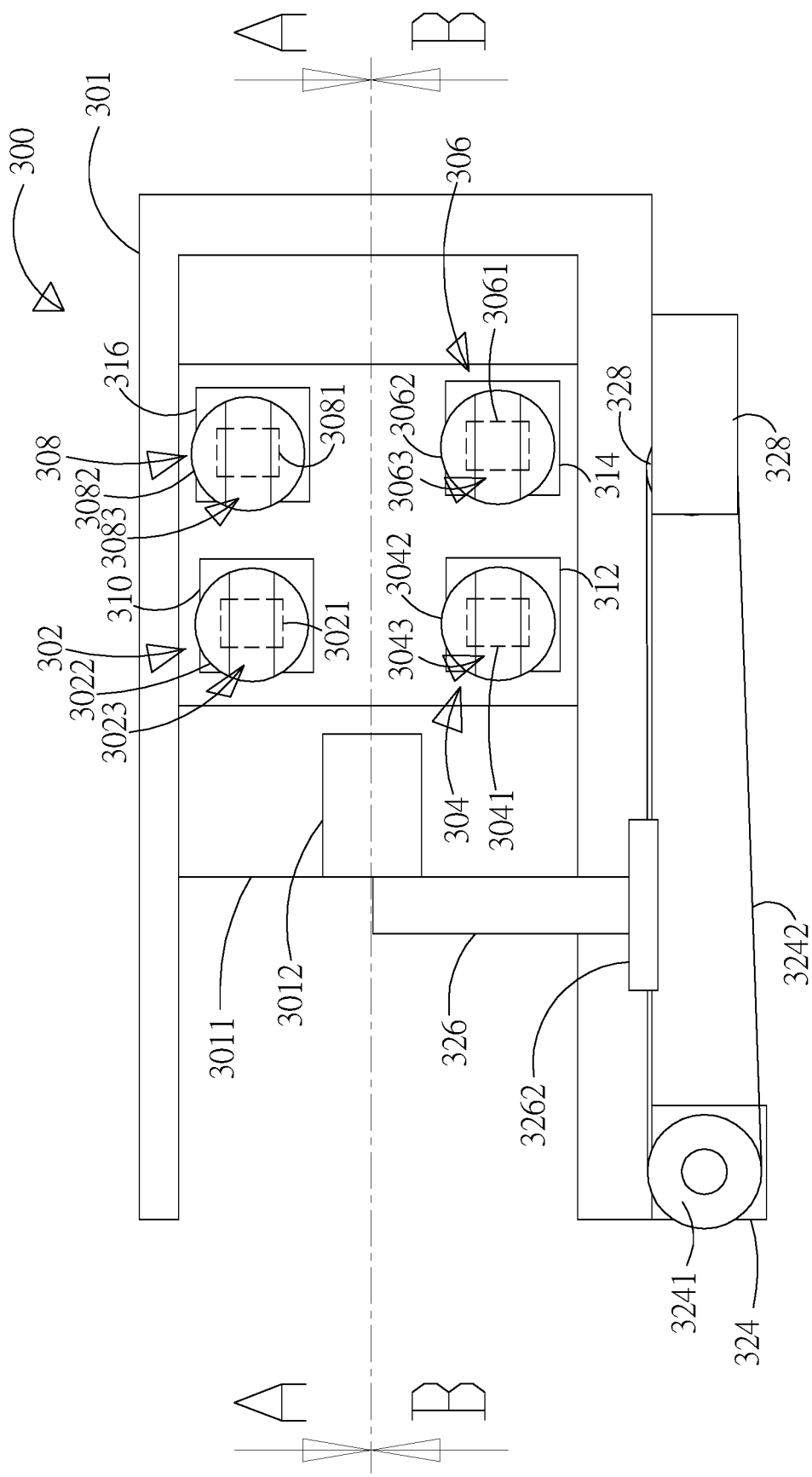
FIG. 2F is a top view of a part of a first robotic arm of an embodiment according to the present invention.
Figure 2G:
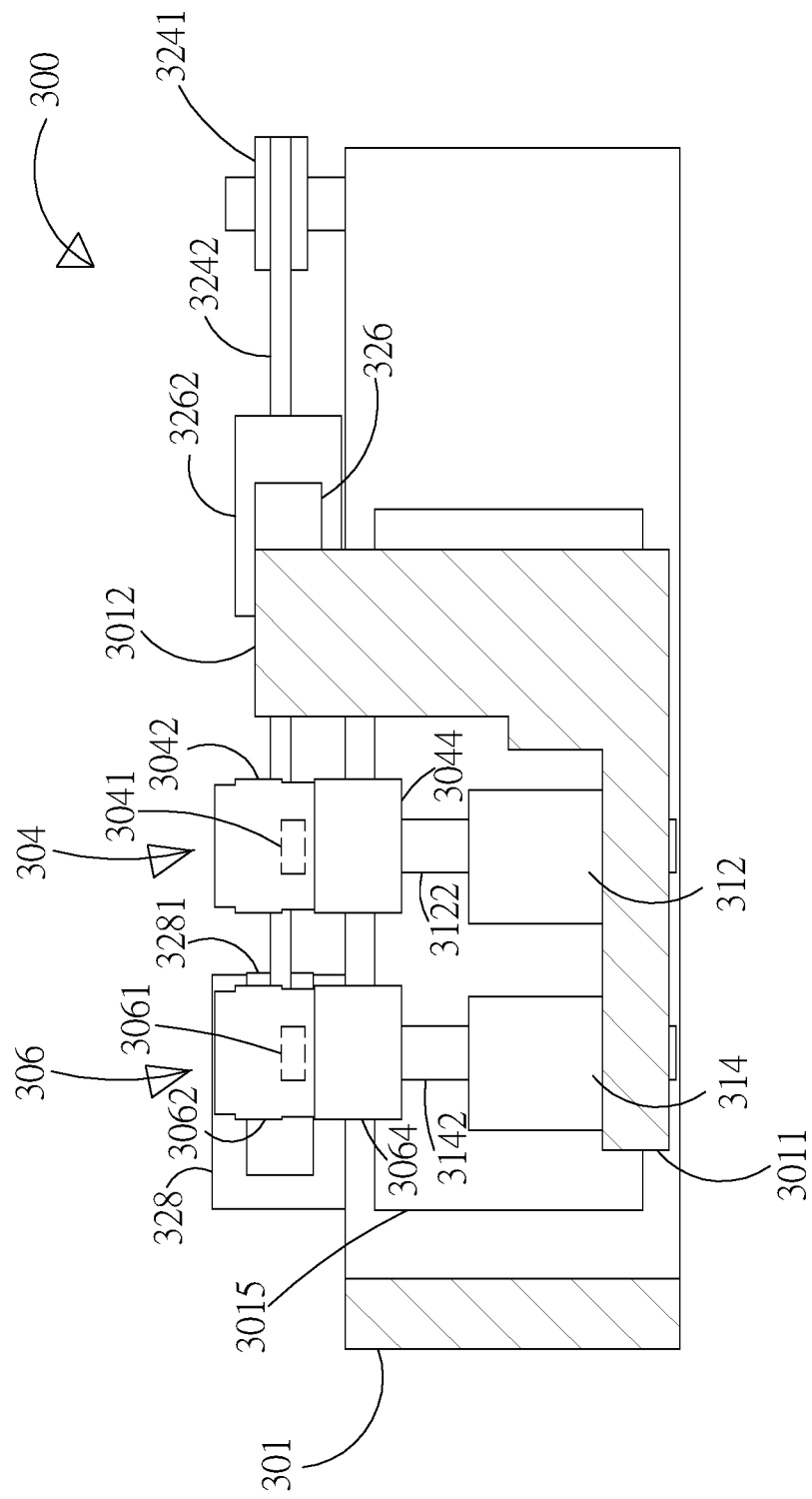
FIG. 2G is a sectional view along line A-A of the embodiment in FIG. 2F according to the present invention.
Figure 2H:
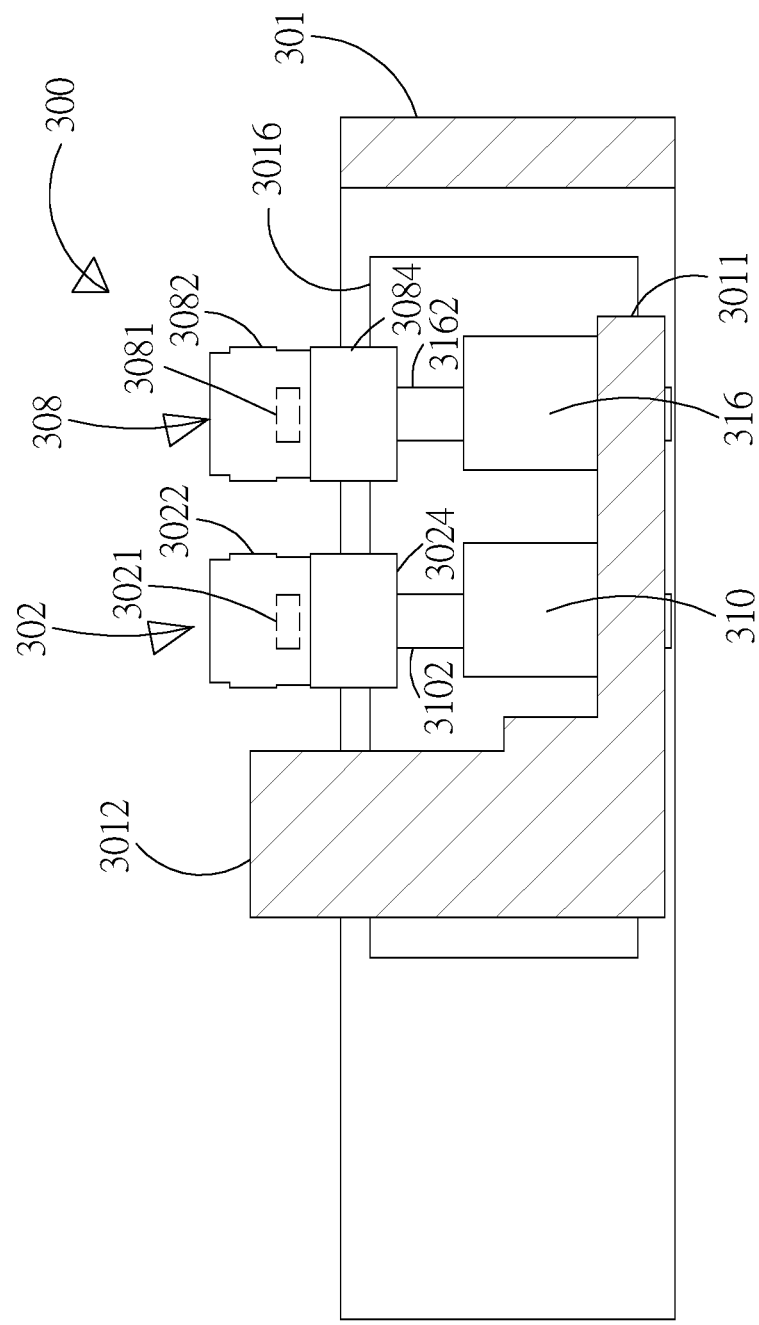
FIG. 2H is a sectional view along line B-B of the embodiment in FIG. 2F according to the present invention.
Figure 3:
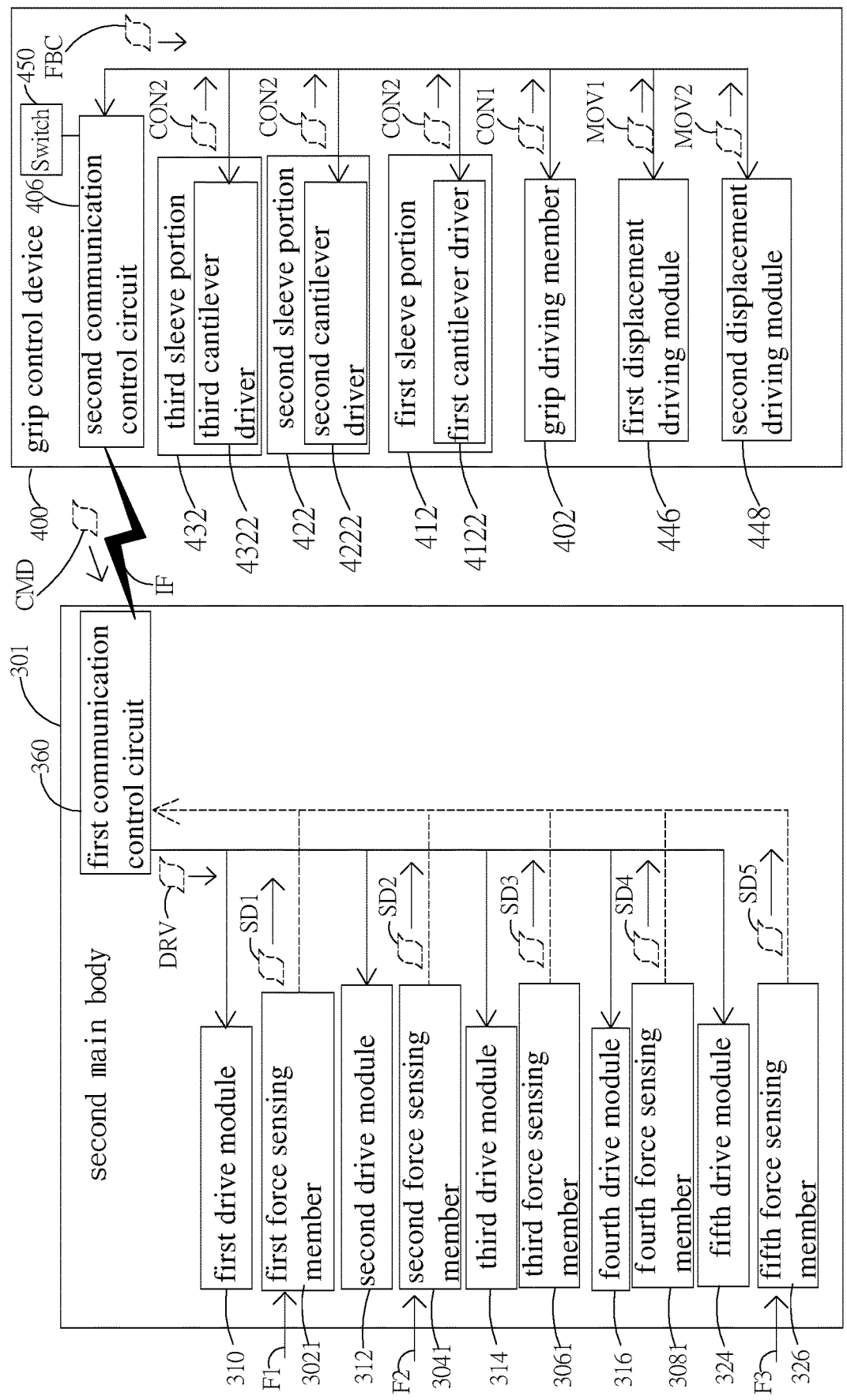
FIG. 3 is a schematic drawing showing sensing of reaction force and signal transmission of an embodiment according to the present invention.
Figure 6A:
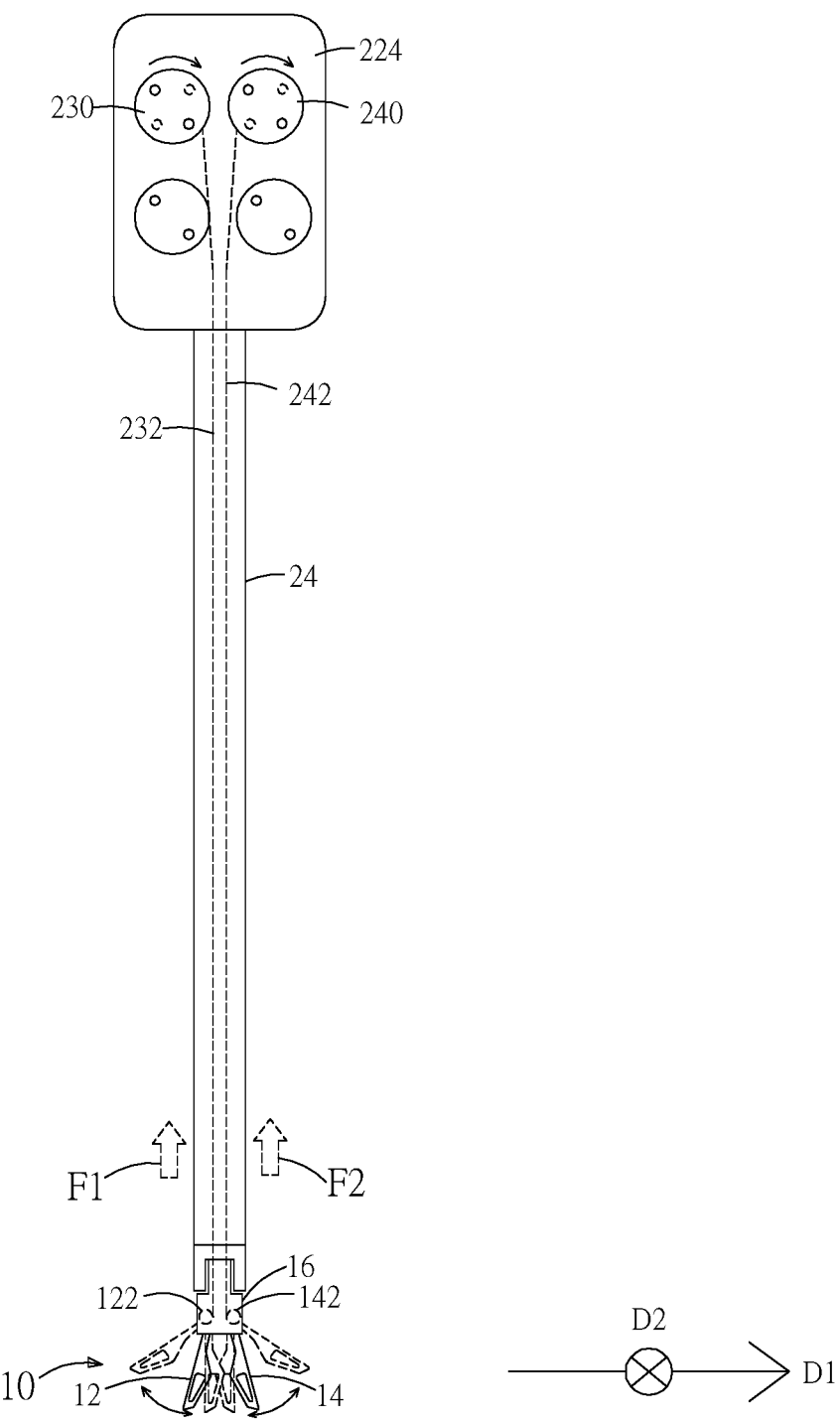
FIG. 6A is a schematic drawing showing a contact module clamping in a first axial direction of an embodiment according to the present invention.

As shown in FIG. 2E and FIG. 3, the first robotic arm 300 further includes a second main body 301 and a second force sensing member 3041 disposed on one side of the second shaft member 304 and linked to the second shaft member 304. The first shaft member 302 and the second shaft member 304 are mounted in the second main body 301 and adjacent to each other. In this embodiment, the second shaft member 304 drives the second force sensing member 3041 to detect a second reaction force F2 and generate a second sensing signal SD2. The second reaction force F2 is transmitted from the second contact member 14 to the second force sensing member 3041 through the second transmission connecting member 242, the second transmission member 240, and the second shaft member 304, as shown in FIG. 2C, FIG. 3, and FIG. 6A. Moreover, the first reaction force F1 is transmitted from the first contact member 122 through the first transmission connecting member 232, the first transmission member 230, and the first shaft member 302. As shown in FIG. 2A, FIG. 2C, FIG. 2D, FIG. 2G, FIG. 3, and FIG. 6A, the first shaft member 302 and the second shaft member 304 respectively drives the first contact member 12 and the second contact member 14 to swing through the first transmission member 230 and the second transmission member 240. While the first contact member 12 and the second contact member 14 being stopped, the first reaction force F1 and the second reaction force F2 are generated. Then the first reaction force F1 is transferred to the first force sensing member 3021 through the first transmission connecting member 232, the first transmission member 230, and the first shaft member 302 while the second reaction force F2 is transferred to the second force sensing member 3041 through the second transmission connecting member 242, the second transmission member 240, and the second shaft member 304. Thereby the first force sensing member 3021 and the second force sensing member 3041 respectively generate the first sensing signal SD1 and the second sensing signal SD2 which are sent to the first communication control circuit 360.

The first reaction force F1 becomes a pull force, tensile force, thrust force or pressure acted on the first force sensing member 3021 so that the first force sensing member 3021 generates a voltage signal or a current signal. In this embodiment, the pull force, the tensile force, the thrust force or the pressure detected by the first force sensing member 3021 is converted into a voltage or current signal used as the first sensing signal SD1 while the first force sensing member 3021 being driven. Similarly, the tensile force, the thrust force or the pressure detected by the second force sensing member 3041 is converted into a voltage or current signal used as the second sensing signal SD2 while the second force sensing member 3041 being driven.

Furthermore, refer to FIG. 2E-2H, FIG. 3, and FIG. 6A, the first robotic arm 300 further incudes a first drive module 310, a second drive module 312, a third drive module 314, and a fourth drive module 316 which are all mounted in the second main body 301. The first shaft member 302, the first force sensing member 3021, the second shaft member 304, the second force sensing member 3041, the first drive module 310, the second drive module 312, the third drive module 314, and the fourth drive module 316 are all arranged at a sliding substrate 3011 which is slidably disposed in the second main body 301. The first drive module 310 drives the first shaft member 302 to rotate through a first driving wheel 3102.

In this embodiment, as shown in FIG. 2D, when the first drive module 310 drives the first shaft member 302 to rotate, the first transmission member 230 is further driven to rotate and transfer motion to the contact module 10 (such as the first contact member 12) through the first transmission connecting member 232. Refer to FIG. 2E-H, the first drive module 310 is disposed on one side of the sliding substrate 3011 and the first force sensing member 3021 is arranged adjacent to a protrusion 3012 of the sliding substrate 3011. A first opening 3015 and a second opening 3016 are mounted to two sides of the second main body 301 correspondingly while the first drive module 310, the second drive module 312, the third drive module 314, and the fourth drive module 316 are disposed on the substrate 3011 inside the second main body 301.

The second drive module 312 which drives the second shaft member 304 to move is linked to the contact module 10 through being linked to the second shaft member 304. And the second force sensing member 3041 detects the second reaction force F2 of the contact module 10. Similarly, the third drive module 314 which drives the third shaft member 306 to move is linked to the contact module 10 through being linked to the third shaft member 306. And a third force sensing member 3061 detects a third reaction force F3 of the contact module 10. The fourth drive module 316 which drives the fourth shaft member 308 to move is linked to the at least one contact module 10 through being linked to the fourth shaft member 308. And a fourth force sensing member 3081 detects a fourth reaction force F4 of the contact module 10. That means the first, second, third and fourth drive modules 310, 312, 314, 316 respectively drive the first, second, third, and fourth shaft members 302, 304, 306, 308 to rotate directly and during the driving process, the first force sensing member 3021, the second force sensing member 3041, the third force sensing member 3061, and the fourth force sensing member 3081 are also driven to work correspondingly.

Still refer to FIG. 2C and FIG. 2D together with FIG. 2E-2H, the third shaft member 306 and the fourth shaft member 308 are respectively connected with and linked to the third drive module 314 and the fourth drive module 316. The third and the fourth shaft members 306, 308 are further linked to the reel member 16 through the control module and the contact module 10 is further driven to rotate axially and swing with a second degree of freedom relative to the rod 24.

In a preferred embodiment, the first robotic arm 300 further includes a fifth drive module 324, a fifth force sensing member 326, and a fifth shaft member 328. The fifth drive module 324 and the fifth shaft member 328 are disposed on one side of the second main body 301 while the fifth force sensing member 326 is arranged at one side of the fifth drive module 324 and connected with the protrusion 3012 of the sliding substrate 3011. The fifth drive module 324 drives a power transmission member 3242 through a fifth driving wheel 3241 while the power transmission member 3242 is wound around the fifth driving wheel 3241 of the fifth drive module 324, a connection block 3262 of the fifth force sensing member 326, and a linked wheel 3281 of the fifth shaft member 328. The second main body 301 is connected with the fifth force sensing member 326 by the sliding substrate 3011. The fifth drive module 324 drives the sliding substrate 3011 to have a displacement through the fifth force sensing member 326.

The first drive module 310, the second drive module 312, the third drive module 314, the fourth drive module 316, and the fifth drive module 324 can be a swing motor driver or an integrated motor driver.

Figure 2I:
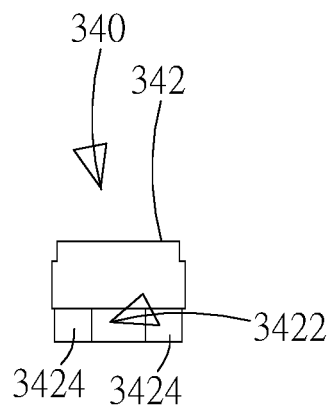
FIG. 2I is a side view of a shaft member of an embodiment according to the present invention.
Figure 2I:
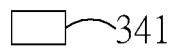
Figure 2I:
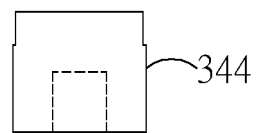
Figure 2I:
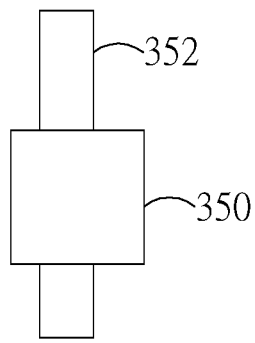
Figure 2J:
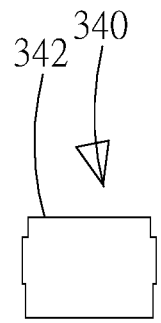
FIG. 2J is another side view of a shaft member of an embodiment according to the present invention.
Figure 2J:
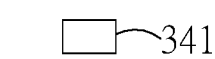
Figure 2J:
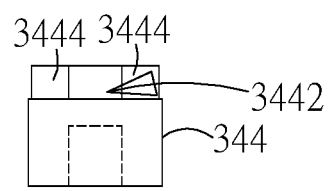
Figure 2J:
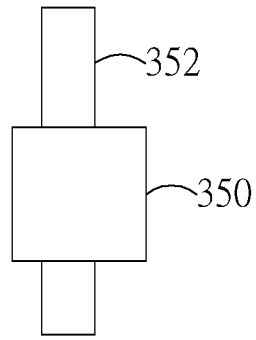

Refer to FIG. 2I and FIG. 2J, a shaft member 340 such as the first shaft member 302, the second shaft member 304, the third shaft member 306, and the fourth shaft member 308 includes a force sensing member 341, an upper transmission member 342, and a lower transmission member 344 which is connected to a driving shaft 352 of a drive module 350. The upper transmission member 342 is provided with an upper connecting recess 3422 and two upper connection surfaces 3424 while the lower transmission member 344 is provided with a lower connecting recess 3442 and two lower connection surfaces 3444. By the two upper connection surfaces 3424 and the two lower connection surfaces 3444 disposed correspondingly to each other, the upper connecting recess 3422 and the lower connecting recess 3442 form a mounting space for the force sensing member 341. The force sensing member 341 is mounted in the mounting space to generate sensing signals according to external forces in parallel and relative to each other through the upper transmission member 342 and the lower transmission member 344.

Figure 2K:
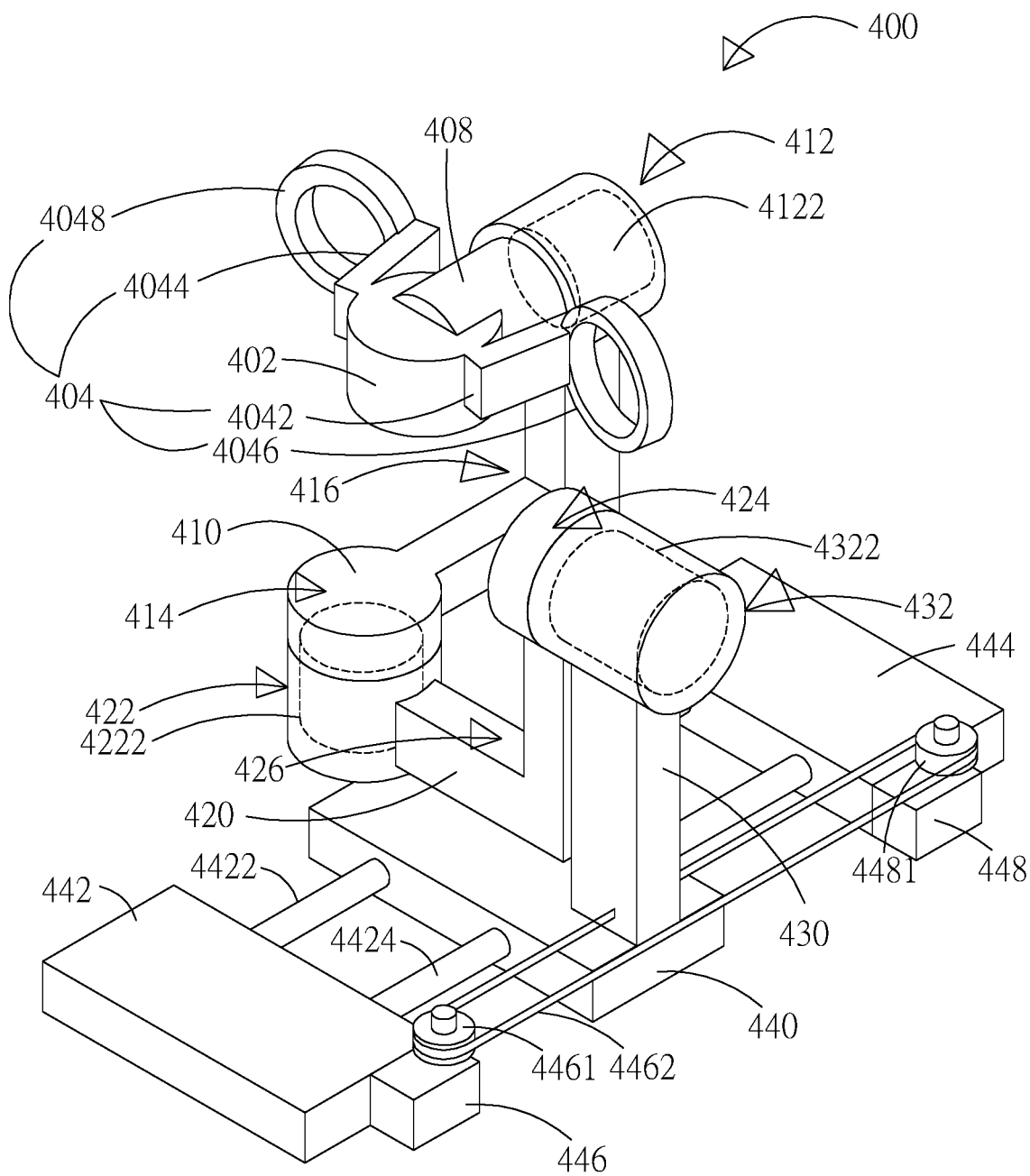
FIG. 2K is a schematic drawing showing structure of a grip control device of an embodiment according to the present invention.
Figure 2L:
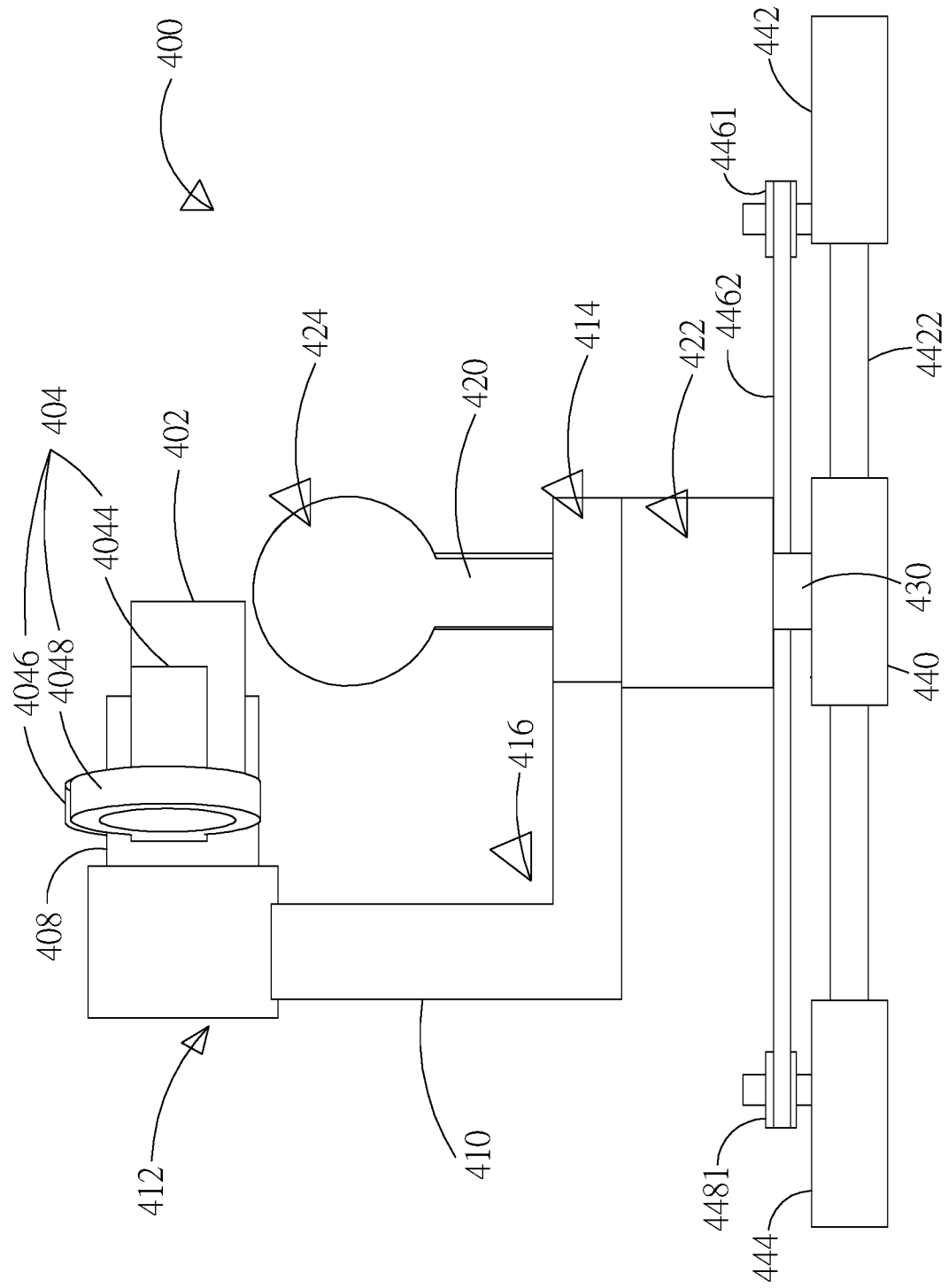
FIG. 2L is a side view of a grip control device of an embodiment according to the present invention.
Figure 2M:
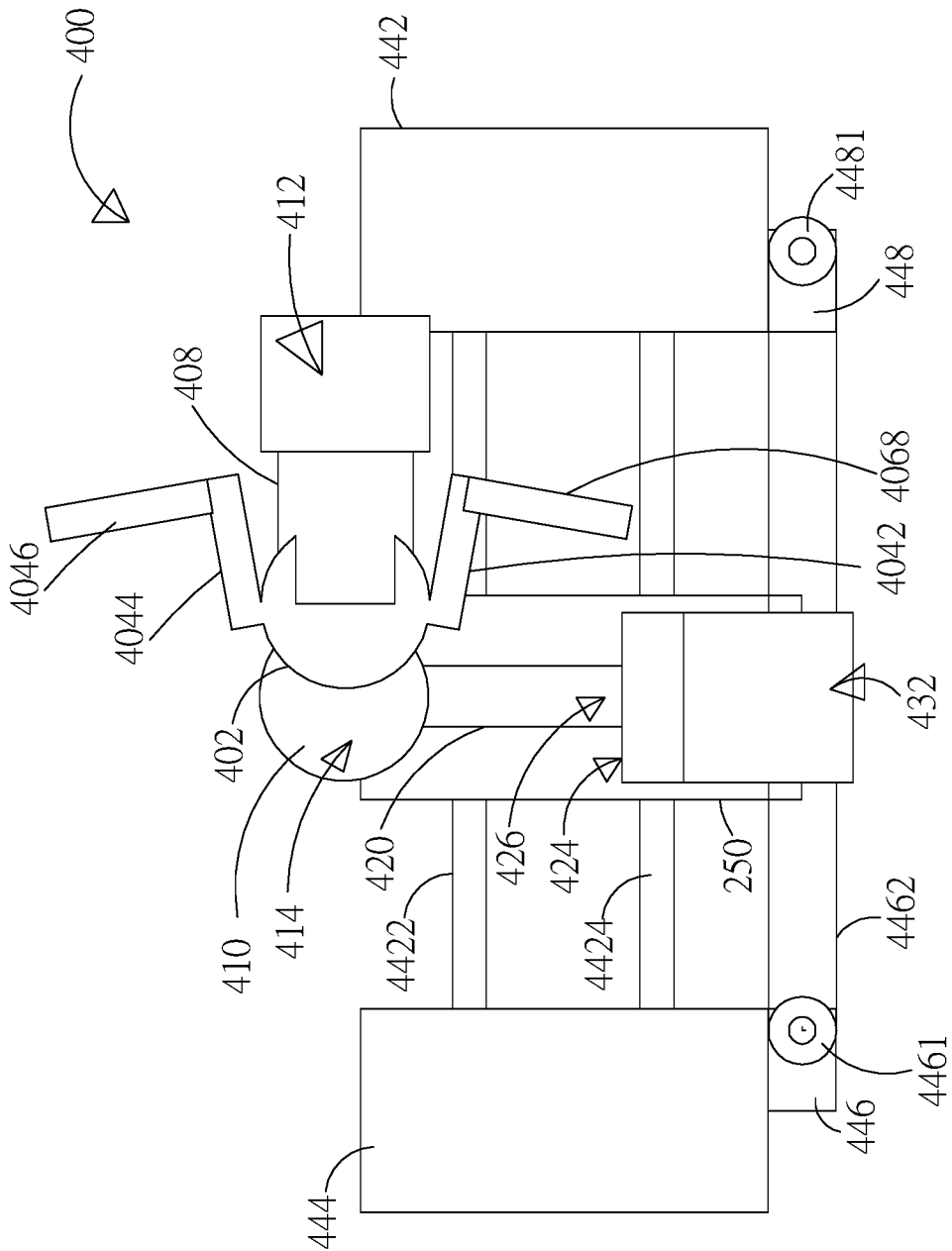
FIG. 2M is a top view of a grip control device of an embodiment according to the present invention.

As shown in FIG. 2K-2M, the grip control device 400 includes a plurality of cantilevers (such as a first cantilever 410, second cantilever 420, and a third cantilever 430 in this embodiment), a control base 440, and two displacement driving module 446, 448. The grip portion 404 further includes a first clamping member 4042 provided with a first loop 4046 and a second clamping member 4044 provided with a second loop 4048. The grip driving member 402 is connected with a first sleeve portion 412 of the first cantilever 410 by a clamping connecting portion 408. A first connecting portion 414 of the first cantilever 410 and a second connecting portion 424 of the second cantilever 420 are respectively connected with a second sleeve portion 422 of the second cantilever 420 and a third sleeve portion 432 of the third cantilever 430.

These cantilevers 410, 420, and 430 are connected in series and connected with the grip driving member 402. The respective sleeve portions 412, 422, 432 of the respective cantilevers 410 420, 430 are provided with a drive module (such as a first cantilever driver 4122, a second cantilever driver 4222, and a third cantilever driver 4322 shown in FIG. 2K) are mounted in the respective cantilevers 410, 420, and 430 correspondingly. The control base 330 is connected to a rear end of the connected cantilevers 410, 420, and 430. That's a rear end of the third cantilever 430.

A first vertical angle 416 is located between the first sleeve portion 412 and the first connecting portion 414 while a second vertical angle 426 is formed between the second sleeve portion 422 and the second connecting portion 424. Vertical directions of the first vertical angle 416 and the second vertical angle 426 go across each other.

In this embodiment, a first displacement driving module 446 and a second displacement driving module 448 are used as an example. A first displacement driving wheel 4461 of the first displacement driving module 446 and a second displacement driving wheel 4481 of the second displacement driving module 448 is linked to the control base 440 through a displacement linking 4462 for control of displacement variation of the control base 440 between a first plate 442 and a second plate 444. At least one tube is disposed between the first plate 442 and the second plate 444. In this embodiment, a first tube 4422 and a second tube 4424 are inserted through the control base 440. The first displacement driving module 446 transmits power to the displacement linking 4462 through the first displacement driving wheel 4461. Then the second displacement driving wheel 4481 of the second displacement driving module 448 and the control base 440 are further driven to move and the control base 440 is moved to have displacement through the first displacement driving wheel 4461 and the second displacement driving wheel 4481.

In another embodiment, there are no first displacement driving module 446 and the second displacement driving module 448 while a displacement function is directly built in the control base 440. The control base 440 is slidably arranged at the first tube 4422 and the second tube 4424 so that the displacement variation of the control base 440 is controlled between the first plate 442 and the second plate 444.

Refer to FIG. 3, a schematic drawing showing sensing of reaction force and signal transmission of an embodiment is revealed. As shown in the figure, the first robotic arm 300 includes the first drive module 310, the second drive module 312, the third drive module 314, the fourth drive module 316, the fifth drive module 324, the first force sensing member 3021, the second force sensing member 3041, the third force sensing member 3061, and the fourth force sensing member 3081. The first force sensing member 3021, the second force sensing member 3041, the third force sensing member 3061, the fourth force sensing member 3081, and the fifth force sensing member 326 are load cells, able to be used in pull force sensors, torque sensors, tension sensors, or pressure sensors. In this embodiment, pull force sensors are used. The first communication control circuit 360 is mounted in the second main body 301. The first drive module 310, the second drive module 312, the third drive module 314, the fourth drive module 316, the fifth drive module 324, the first force sensing member 3021, the second force sensing member 3041, the third force sensing member 3061, the fourth force sensing member 3081, and the fifth force sensing member 326 are all electrically connected with the first communication control circuit 360.

The second communication control circuit 406 generates a drive control signal CMD sent to the first communication control circuit 360 so that the first communication control circuit 360 provide a drive signal DRV to the first drive module 310, the second drive module 312, the third drive module 314, the fourth drive module 316, and the fifth drive module 324 for driving them to make the first shaft member 302, the second shaft member 304, the third shaft member 306, the fourth shaft member 308 and the fifth shaft member 328 rotate correspondingly.

The first force sensing member 3021, the second force sensing member 3041, the third force sensing member 3061, the fourth force sensing member 3081, and the fifth sensing member 326 are all provided with a sensor for detecting/sensing the first reaction force F1, the second reaction force F2, the third reaction force F3, the fourth reaction force F4, and the fifth reaction force F5 respectively and generating the first sensing signal SD1, the second sensing signal SD2, the third sensing signal SD3, the fourth sensing signal SD4, and the fifth sensing signal SD5 correspondingly. Then the first communication control circuit 360 sends force feedback information FD including the first sensing signal SD1, the second sensing signal SD2, a third sensing signal SD3, a fourth sensing signal SD4, and a fifth sensing signal SD5 to the second communication control circuit 406. Also refer to FIG. 2E to FIG. 2H, the first force sensing member 3021 detects the first reaction force F1 sent back by the first contact member 12 of the contact module 10 through the first shaft member 302 and then generates the first sensing signal SD1 which is sent to the first communication control circuit 360. Similarly, the second force sensing member 3041 detects the second reaction force F2 sent back by the contact module 10 through the second shaft member 304 and then generates the second sensing signal SD2 which is sent to the first communication control circuit 360. The third force sensing member 3061 detects the third reaction force F3 sent back by the contact module 10 through the third shaft member 306 and then generates the third sensing signal SD3 which is sent to the first communication control circuit 360. The fourth force sensing member 3081 detects the fourth reaction force F4 sent back by the contact module 10 through the fourth shaft member 308 and then generates the fourth sensing signal SD4 which is sent to the first communication control circuit 360. The fifth force sensing member 326 detects deformation of the fifth force sensing member 326 itself and generates the fifth reaction force F5 and then further generates the fifth sensing signal SD5 which is sent to the first communication control circuit 360.

The first force sensing member 3021, the second force sensing member 3041, the third force sensing member 3061, the fourth force sensing member 3081, and the fifth sensing member 326 mentioned above are load cells which are a special form of force sensors formed by combination of a strain gauge and bridge circuit. A sensing output (generally a voltage signal) of the load cell is proportional to the force applied to the load cell such as pull force, thrust, tension or pressure. Elastic deformation occurs in the load cell due to gravity load and the strain gauge adhered inside the load cell converts the force/load into voltage signals or current signals proportionally.

Refer to FIG. 2K-2M and FIG. 3, the grip control device 400 further includes the first cantilever driver 4122, the second cantilever driver 4222, the third cantilever driver 4322, the first displacement driving module 446, and the second displacement driving module 448. The second communication control circuit 406 is electrically connected with the grip driving member 402, the first cantilever driver 4122, the second cantilever driver 4222, the third cantilever driver 4322, the first displacement driving module 446, and the second displacement driving module 448. The first cantilever driver 4122, the second cantilever driver 4222, the third cantilever driver 4322 are respectively disposed in the first sleeve portion 412, the second sleeve portion 422, and the third sleeve portion 432.

According to the grip portion 404 linked, the grip driving member 402 generates and sends a corresponding first control drive signal CON1 to the second communication control circuit 406. The first, second and third cantilevers 410, 420, 430 are linked to the first, second and third cantilever drivers 4122, 4222, 4322 for driving the cantilever drivers 4122, 4222, 4322 to generate and send at least one corresponding second control drive signal CON2 to the second communication control circuit 406. That means the first cantilever driver 4122, the second cantilever driver 4222, the third cantilever driver 4322 respectively generate the corresponding second control drive signal CON2 according to the first, second and third cantilevers 410, 420, 430 linked.

The first displacement driving module 446 and the second displacement driving module 448 respectively generate and send a first displacement feedback control signal MOV1 and a second displacement feedback control signal MOV2 to the second communication control circuit 406. According to the above first control drive signal CON1, the second control drive signal CON2, the first displacement feedback control signal MOV1, and the second displacement feedback control signal MOV2, the second communication control circuit 406 generates and sends a corresponding drive control signal CMD to the first communication control circuit 360. Next the second communication control circuit 406 further produces a corresponding feedback control signal FBC according to the force feedback information FD for driving the grip driving member 402, the first cantilever driver 4122, the second cantilever driver 4222, the third cantilever driver 4322, the first displacement driving module 446, and the second displacement driving module 448 to work. Thereby the grip portion 404, the first cantilever 410, the second cantilever 420, the third cantilever 430, and the control base 440 are driven to move.

The first axial direction D1 and the second axial direction D2 mentioned above are defined by a conventional two-dimensional coordinate, Cartesian coordinate system (système de coordonnées cartésiennes, also called a rectangular coordinate system) which is an orthogonal coordinate named after the French mathematician Rene Descartes. The 2D rectangular coordinate system is defined by two perpendicular oriented lines (axes) and the point they meet is the origin. For any point in a plane, the coordinates of the point are defined by a line drawn through the point and perpendicular to each axis and the positions where the lines meet the axes are interpreted as numbers.

The rectangular coordinate system can also be applied to three-dimensional space and higher dimensions. One more coordinate axis, z-axis, perpendicular to the x-axis and y-axis is added in the original 2D coordinate. The 3D rectangular coordinate system is obtained once the three axes are unable to match the right hand rule. The three axes, z-axis, x-axis, and y-axis, have a common point of intersection, called the origin. The rectangular coordinates of a point in three dimensions can be represented by a triplet of numbers (x, y, z).

Figure 4A:
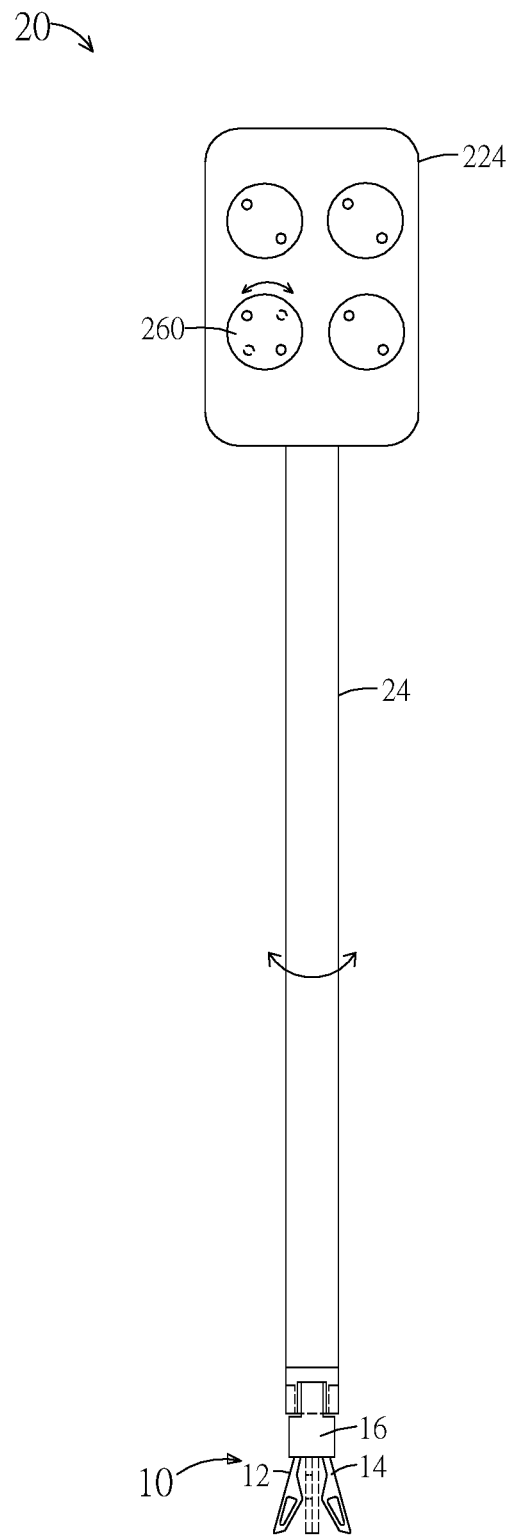
FIG. 4A is a schematic drawing showing a contact module rotated around an axial direction of a rod of an embodiment according to the present invention.
Figure 4B:
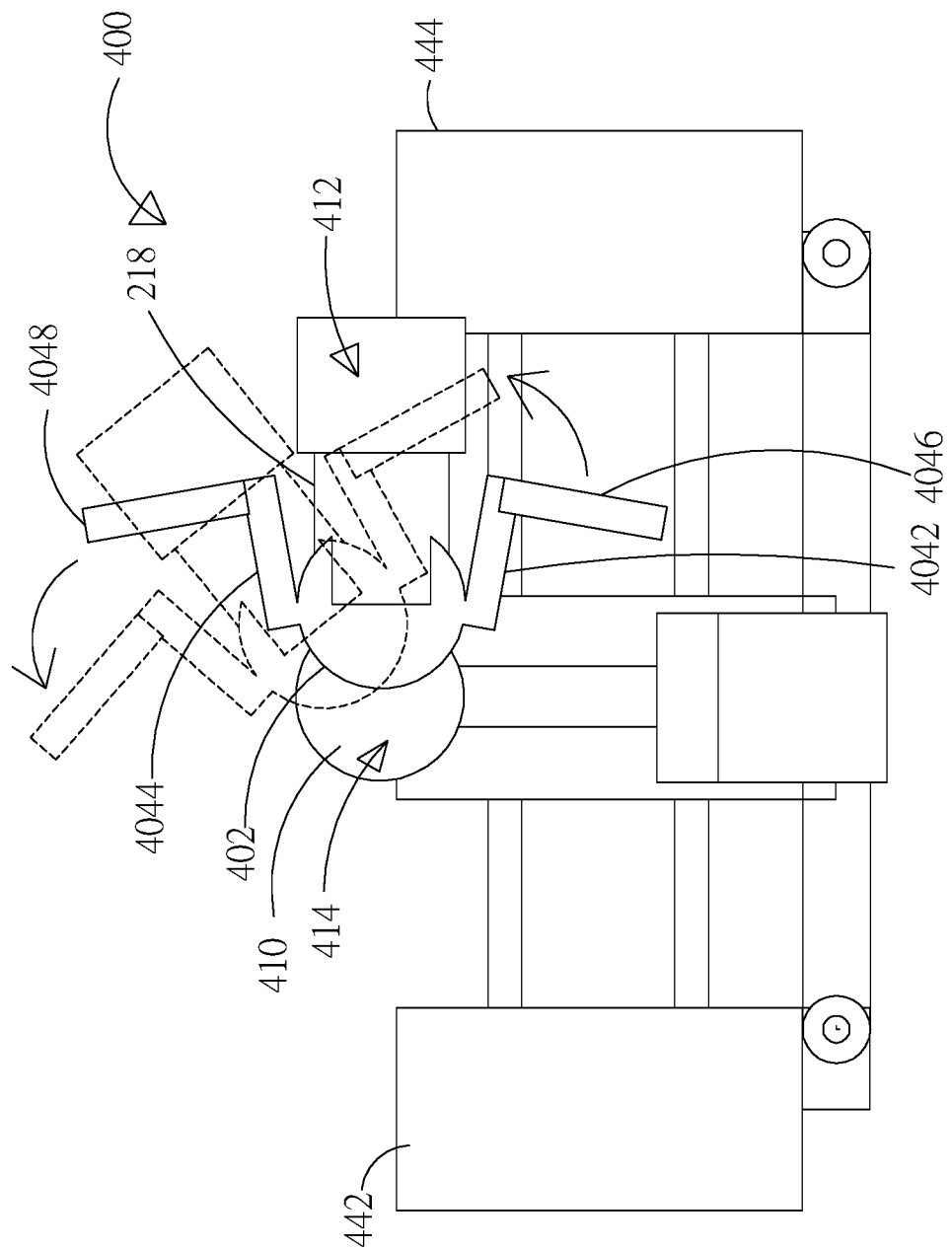
FIG. 4B is a schematic drawings showing a grip control device swinging horizontally of an embodiment according to the present invention.

Next refer to FIG. 4A and FIG. 4B, schematic drawings showing a contact module rotated around a rod axially (an axial direction of a rod) and a grip control device swinging horizontally of an embodiment are revealed. As shown in FIG. 2B, in the control connection module 20 of this embodiment, the first transmission member 230 is inserted through the bottom plate 224 to an outer side of the bottom plate 224 while the fourth transmission member 260 is able to rotate for driving the fourth transmission connecting member 262. When the fourth transmission member 260 rotates, the fourth transmission connecting member 262 is driven to make the contact module 10 rotate around an axial direction of the rod 24. That means the contact module 10 rotates around a central axis C of the rod 24. Also refer to FIG. 3, correspondingly, the first cantilever 410 is swinging horizontally with respect of the second cantilever 420 of the grip control device 400 so that the second cantilever driver 4222 generates the corresponding second control drive signal CON2 by which the axial rotation of the rod 24 is controlled. To put it simply, the user operates the grip control device 400 to let the first cantilever 410 have horizontal swinging with respect to the second cantilever 420. Put differently, the user operates the grip control device 400 to make the first cantilever 410 swing horizontally with respect to the second cantilever 420 for control of axial rotation of the rod 24.

Figure 5A:
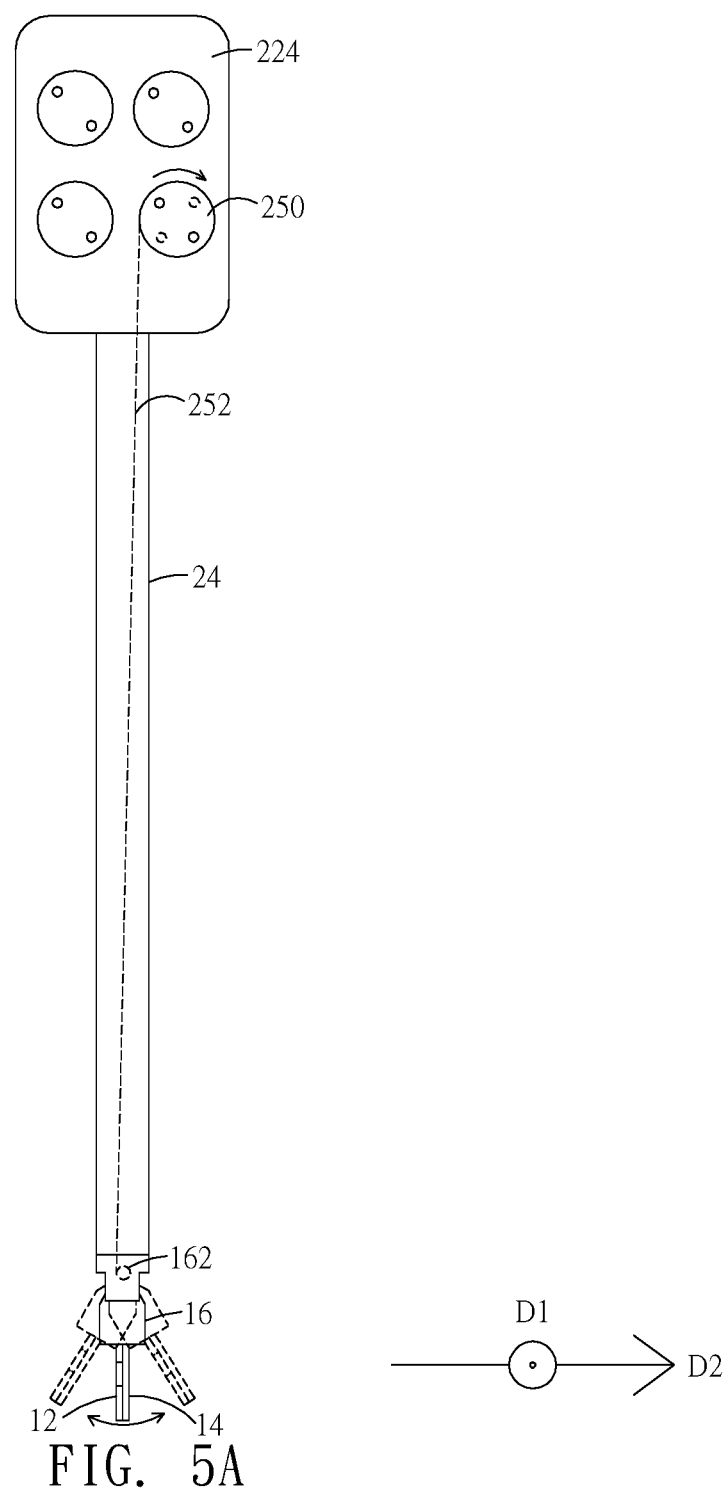
FIG. 5A is a schematic drawing showing a contact module swinging in a second axial direction of an embodiment according to the present invention.

Moreover, refer to FIG. 5A and FIG. 5B, schematic drawings showing a contact module swinging in a second axial direction and a grip control device swinging vertically of an embodiment are revealed. As shown in figure, in the control connection module 20 of this embodiment, the third transmission member 250 is connected with a third reel part 162 through the third transmission connecting member 252 and further driving the reel member 16 of the contact module 10 to move from a center of the rod 24 to the second axial direction D2 (refer to dotted line shown in FIG. 5A). That means the third transmission connecting member 252 on the third transmission member 250 is also driven (as shown in FIG. 2B) to move when the third transmission member 250 is rotating. Thereby the reel member 16 of the contact module 10 move back and forth from the central axis C of the rod 24 to the second axial direction D2. Also refer to FIG. 3, the first and the second cantilevers 410, 420 of the grip control device 400 swing vertically with respect to the third cantilever 430 so that the third cantilever driver 4322 generates the corresponding second control drive signal CON2. Thereby the reel member 16 is controlled to move in the second axial direction D2. Put simply, the user operates the grip control device 400 to make the first and the second cantilevers 410, 420 swing vertically with respect to the second cantilever 420 for control of the reel member 16 to move in the second axial direction D2.

Figure 6B:
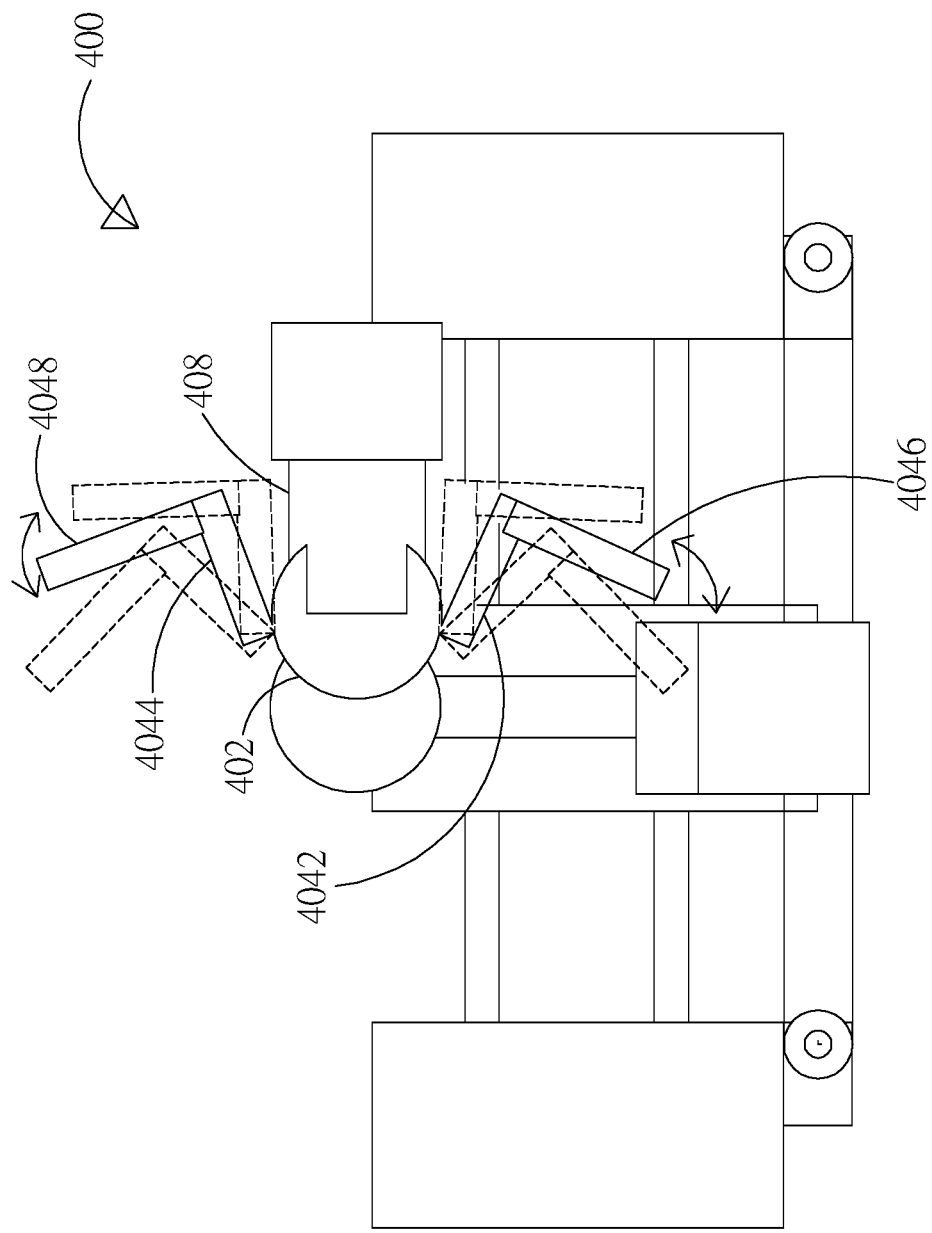
FIG. 6B is a schematic drawings showing a grip control device being hold for control of clamping of an embodiment according to the present invention.

Refer to FIG. 6A and FIG. 6B, schematic drawings showing a contact module clamping in a first axial direction and clamping control of a grip control device of an embodiment are revealed. As shown in the figure, in the control connection module 20 of this embodiment, the first transmission member 230 and the second transmission member 240 drive the first and the second contact members 12, 14 of the contact module 10 to move in the first axial direction D1 (refer to dotted line shown in FIG. 6A). When the first and the second transmission members 230, 240 rotate, the first and the second transmission connecting member 232, 242 (as shown in FIG. 2B) are driven to move so that the first and the second contact members 12, 14 linked are also moved to clamp in the first axial direction D1. Also refer to FIG. 3, the grip portion 404 of the grip control device 400 swings horizontally with respect to the grip driving member 402 so that the grip driving member 402 generates the corresponding first control drive signal CON1. Thereby the first contact member 12 and the second contact member 14 are controlled to move in the first axial direction D1. In other words, the user operates the grip control device 400 to make the grip portion 404 swing horizontally with respect to the grip driving member 402 for control of the first contact member 12 and the second contact member 14 to move in the first axial direction D1.

Figure 6C:
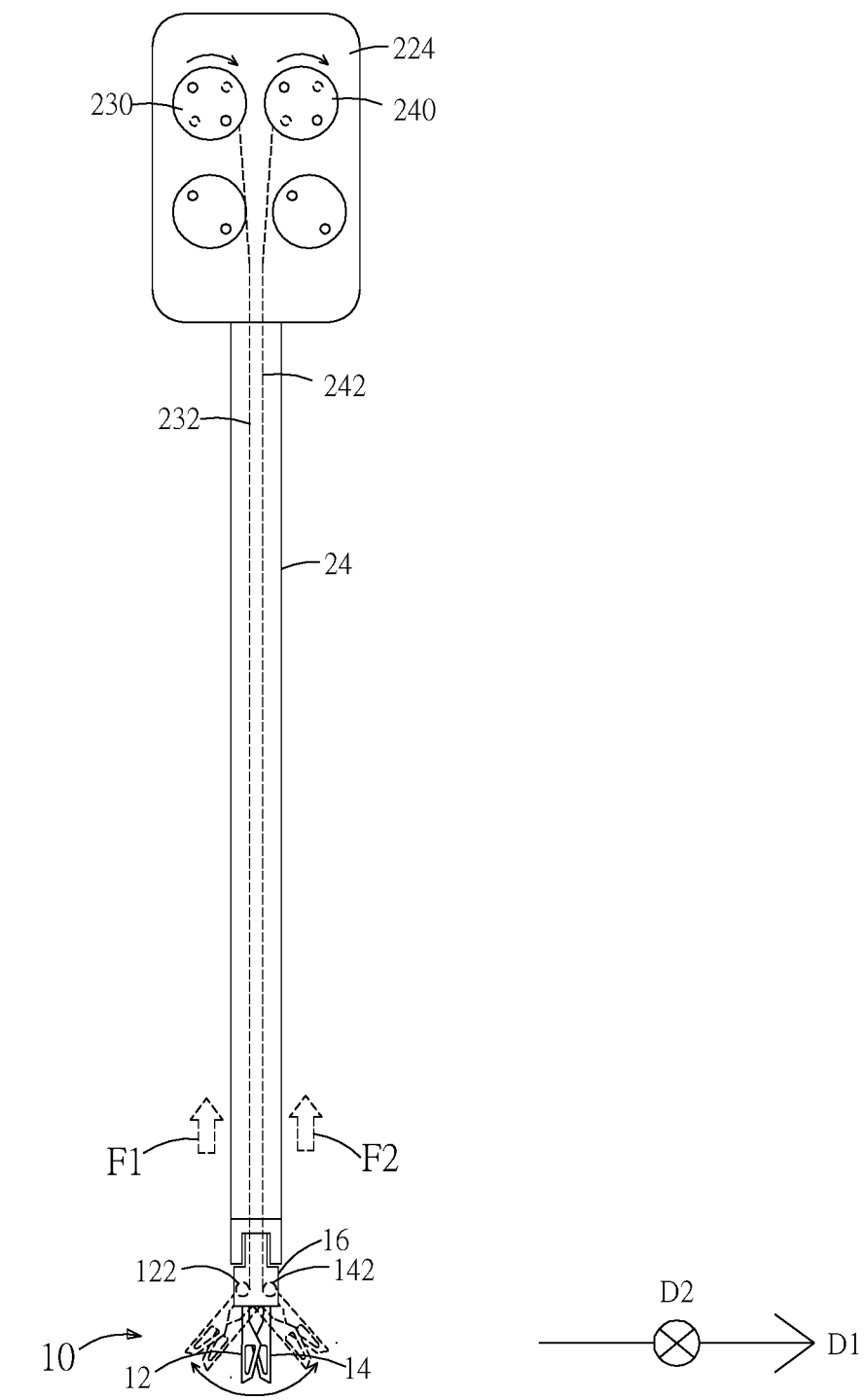
FIG. 6C is a schematic drawing showing a contact module swinging in a first axial direction of an embodiment according to the present invention.

Refer to FIG. 6C, a schematic drawing showing a contact module swinging in a first axial direction is revealed. As shown in the figure, the first transmission member 230 and the second transmission member 240 drive the first contact member 12 and the second contact member 14 of the contact module 10 to move in the first axial direction D1 (refer to dotted line shown in FIG. 6A). That means when the first and the second transmission members 230, 240 rotates, the first and the second transmission connecting member 232, 242 (as shown in FIG. 2B) are driven to move so that the first and the second contact members 12, 14 linked swing in the first axial direction D1. The control way of this embodiment is the same as the embodiment shown in FIG. 6B in combination with FIG. 3. In this embodiment, the contact module 10 is a holder formed by the first contact member 12 and the second contact member 14. For example, the contact module 10 can be a file, a scraper, a saw, a pair of scissors, or a screwdriver. In this embodiment, the scissor is used as the contact module 10.

Back to FIG. 1, the surgical robot 1 according to the present invention further includes a second robotic arm 192 which has one end connected with the other end of the first robotic arm 300 by a first driving member 191. A driving motor inside the first driving member 191 drives the end of the first robotic arm 300 connected to move pivotally with respect to a vertical direction at the end of the second robotic arm 192 so that the first robotic arm 300 swings. In other words, the first driving member 191 is arranged at one end of the second robotic arm 192 and pivotally connected with the other end of the first robotic arm 300.

The other end of the second robotic arm 192 is connected with one end of a third robotic arm 194 by a second driving member 193. Similarly, a driving motor inside the second driving member 193 drives the other end of the second robotic arm 192 connected to move pivotally relative to a vertical direction at the end of the third robotic arm 194 so that the second robotic arm 192 swings. In other words, the second driving member 193 is arranged at one end of the third robotic arm 194 and pivotally connected with the other end of the second robotic arm 192.

The other end of the third robotic arm 194 is connected with one end of a fourth robotic arm 196 by a third driving member 195. The third driving member 195 drives the other end of the third robotic arm 194 connected to swing in a horizontal direction relative to the fourth robotic arm 196. That means the third driving member 195 drives the other end of the third robotic arm 194 to rotate pivotally with respect to a horizontal direction of the fourth robotic arm 196. In other words, the third driving member 195 is arranged at one end of the fourth robotic arm 196 and pivotally connected with the other end of the third robotic arm 194.

In addition, the other end of the fourth robotic arm 196 is pivotally connected with a fourth driving member 197 which is disposed on a control base 198. Thereby the other end of the fourth robotic arm 196 is swinging relative to a horizontal direction of the control base 198.

Thus the first driving member 191 and the second driving member 193 are in the same driving direction while the third driving member 195 and the fourth driving member 197 are in the same driving direction. The driving direction of the first and the second driving members 191, 193 is different from the driving direction of the third and the fourth second driving members 195, 197.

Therefore, it is learned that the surgical robot 1 is provided with the first robotic arm 300, the second robotic arm 192, the third robotic arm 194, and the fourth robotic arm 196 which are respectively driven by the first driving member 191, the second driving member 193, the third driving member 195, and the fourth driving member 197 correspondingly to make the surgical robot 1 swing in a way like having a plurality of joints. Thereby the surgical robot 1 controls movement patterns of the control connection module 20 and further controls delicate operation of the contact module 10.

As shown in FIG. 7A-7D, the first robotic arm 300 provides corresponding linear control by the force sensing members 3021, 3041, 3061, 3081 which detects resistance from the contact module 10. According to curves of signals in the figures, it is learned that the first robotic arm 300 provides linear operation by detection results of the force sensing members 3021, 3041, 3061, 3081 so that linear compensation is applied by the system based on the signal curves and relative rotation angles. The linear compensation mentioned above is carried out by the first communication control circuit 360 and the second communication control circuit 406 according to the force applied to the contact module 10 and the first reaction force F1, the second reaction force F2, the third reaction force F3, and the fourth reaction force F4 detected by the respective force sensing members 3021, 3041, 3061, 3081 correspondingly.

Figure 7A:
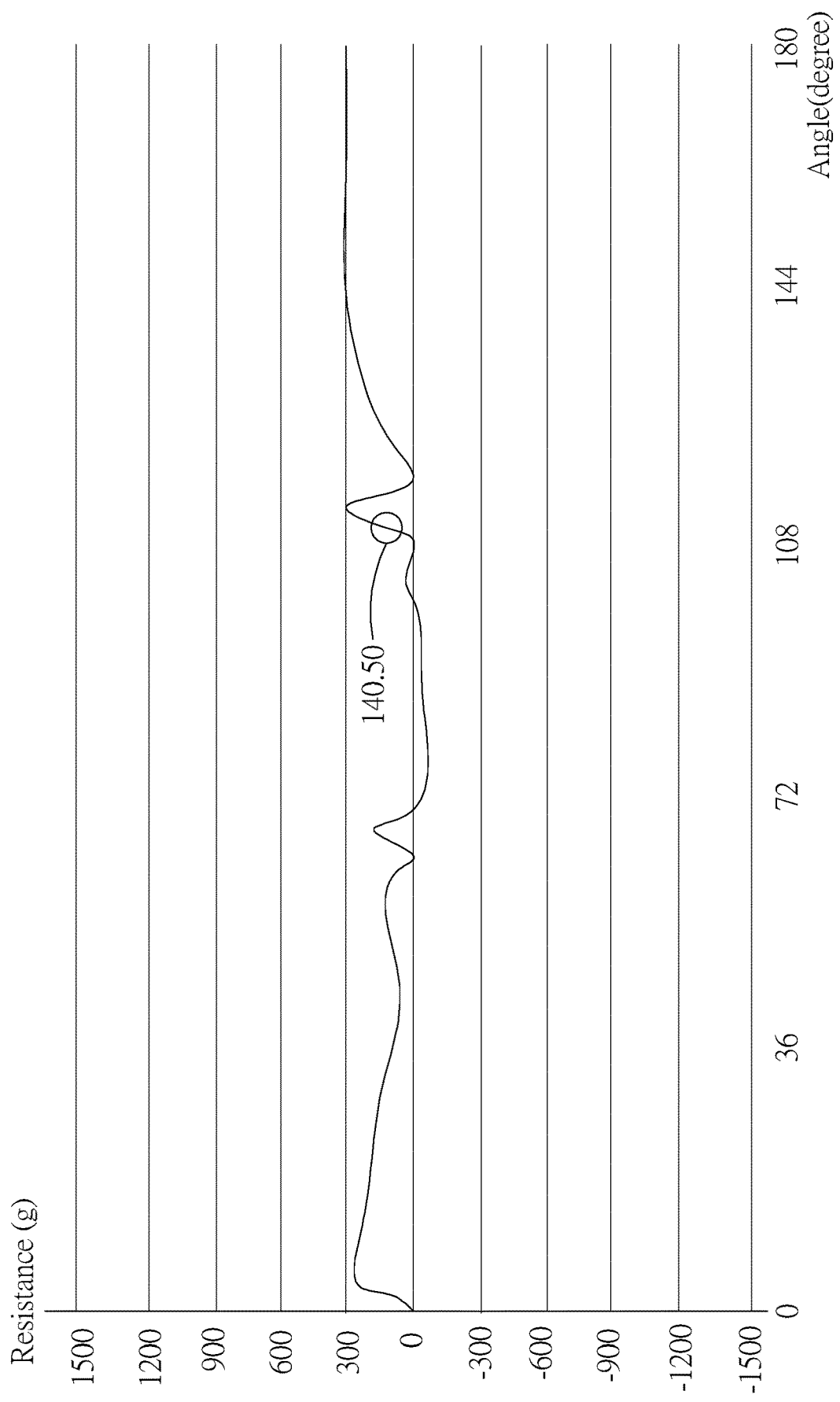
FIG. 7A is a curve of a fourth sensing signal during axial rotation of a contact module in accordance with a rod of an embodiment according to the present invention.
Figure 7B:
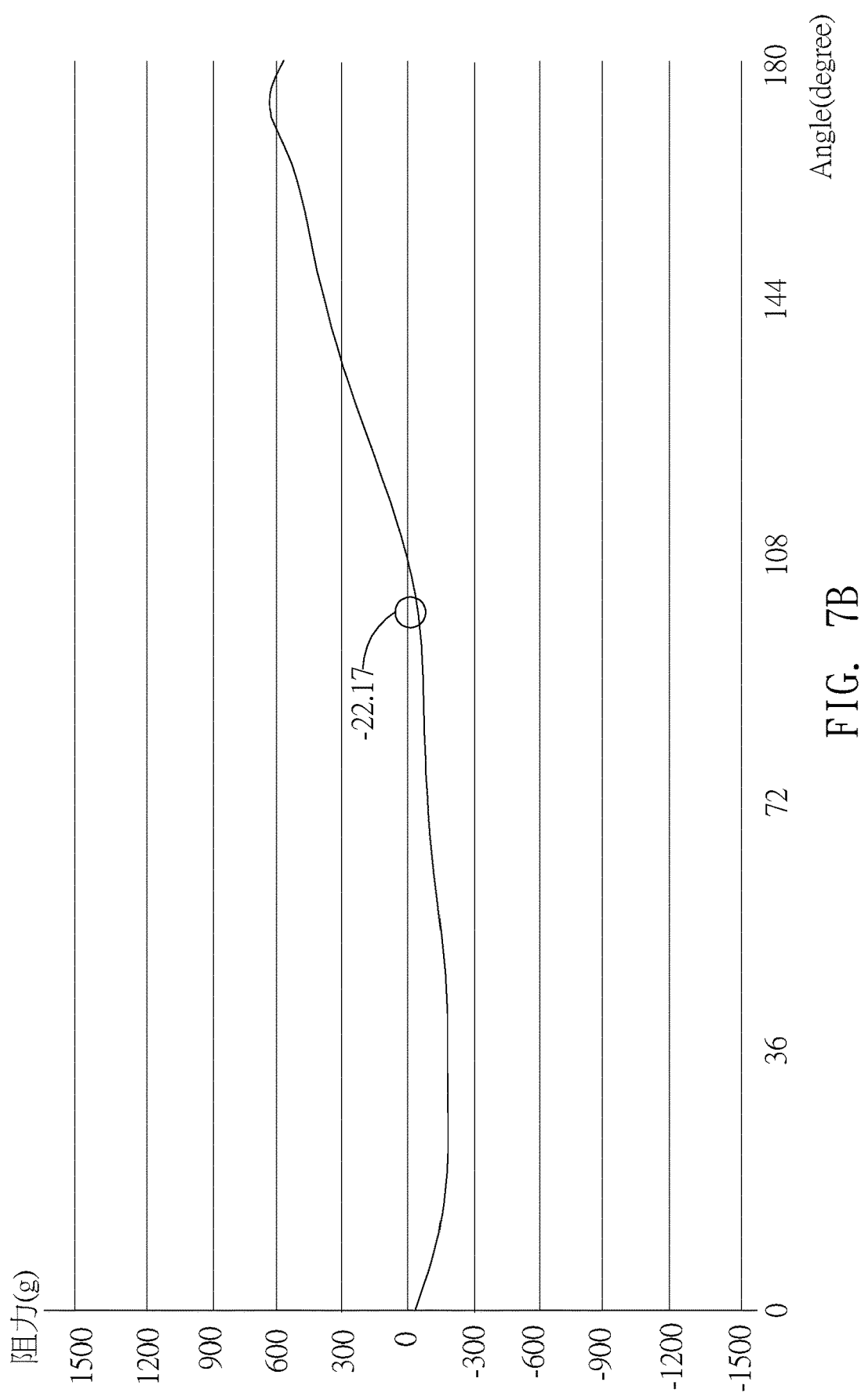
FIG. 7B is a curve of a third sensing signal during swinging of a contact module in a second axial direction of an embodiment according to the present invention.

Refer to FIG. 4A and FIG. 7A, when the contact module 10 rotates from 0 degree to 180 degrees in accordance with the axial direction of the rod 24, the fourth reaction force F4 detected by the fourth force sensing members 3081 falls in a range of −100 g-300 g. Thus at least one of by the first communication control circuit 360 and the second communication control circuit 406 provides a corresponding compensation according to the signal curve shown in FIG. 7A to avoid improper force applied by the contact module 10. As shown in FIG. 5A and FIG. 7B, when the reel member 16 of the contact module 10 moves from the center of the rod 24 to the second axial direction D2, the third reaction force F3 detected by the third force sensing members 3061 falls in a range of −300 g-600 g along with the rotation angle ranging from 0 to 180 degrees. Thus at least one of by the first communication control circuit 360 and the second communication control circuit 406 provides a corresponding compensation according to the signal curve shown in FIG. 7B to avoid improper force applied by the contact module 10.

Figure 7C:
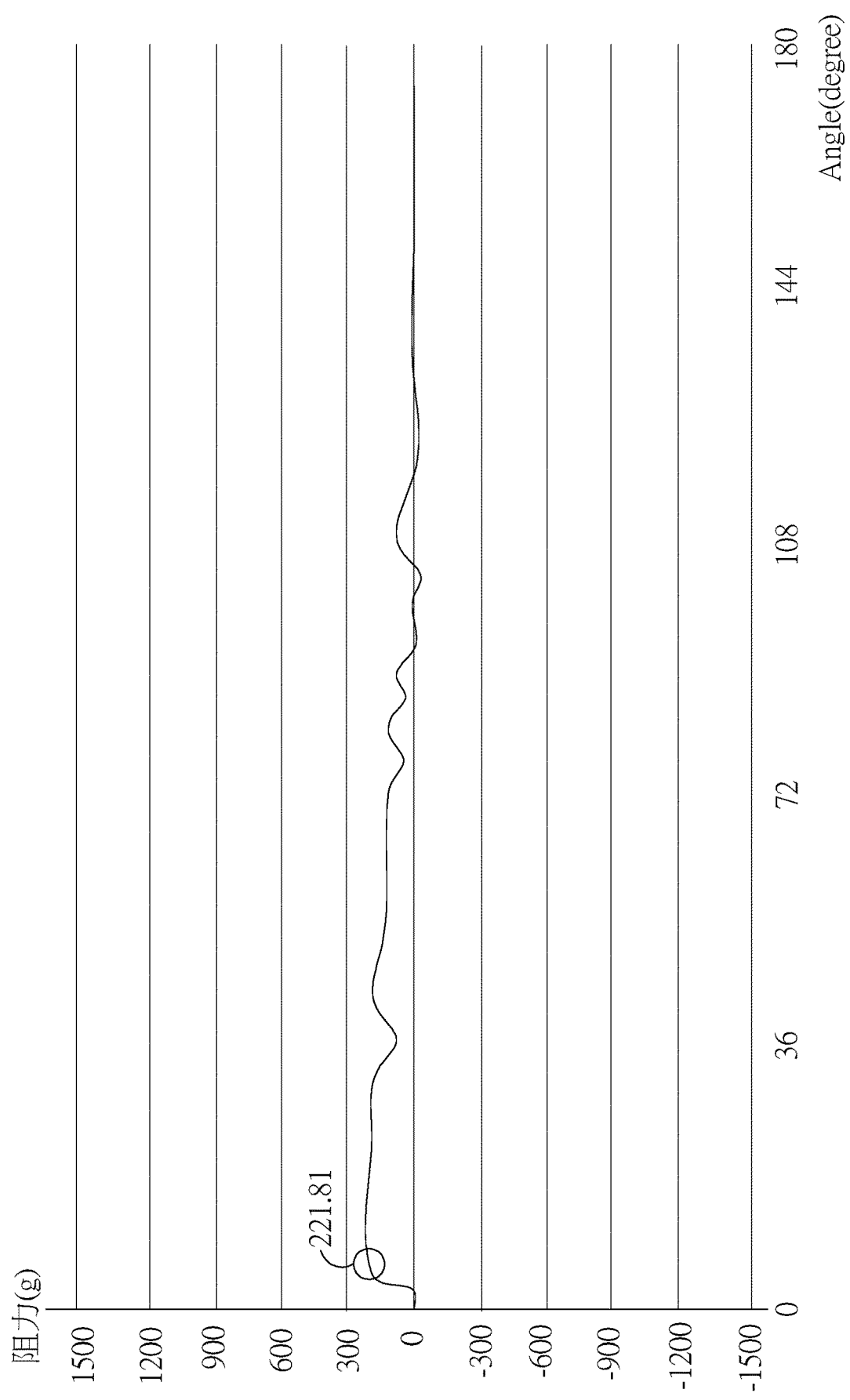
FIG. 7C is a curve of a first sensing signal and a second sensing signal during clamping of a contact module of an embodiment according to the present invention.

FIG. 6A and FIG. 7C, when the contact module 10 clamps in the first axial direction D1, an average value of the first reaction force F1 detected by the first force sensing members 3021 and the second reaction force F2 detected by the second force sensing members 3041 falls in a range of −100 g-300 g along with the rotation angle ranging from 0 to 180 degrees. Thus at least one of the first communication control circuit 360 and the second communication control circuit 406 provides a corresponding compensation according to the signal curve shown in FIG. 7C to avoid improper force applied by the contact module 10. As shown in FIG. 6C and FIG. 7B, when the contact module 10 swings in the first axial direction D1, an average value of the first reaction force F1 detected by the first force sensing members 3021 and the second reaction force F2 detected by the second force sensing members 3041 falls in a range of −300 g-0 g along with the rotation angle ranging from 0 to 180 degrees. Thus at least one of the first communication control circuit

Figure 7D:
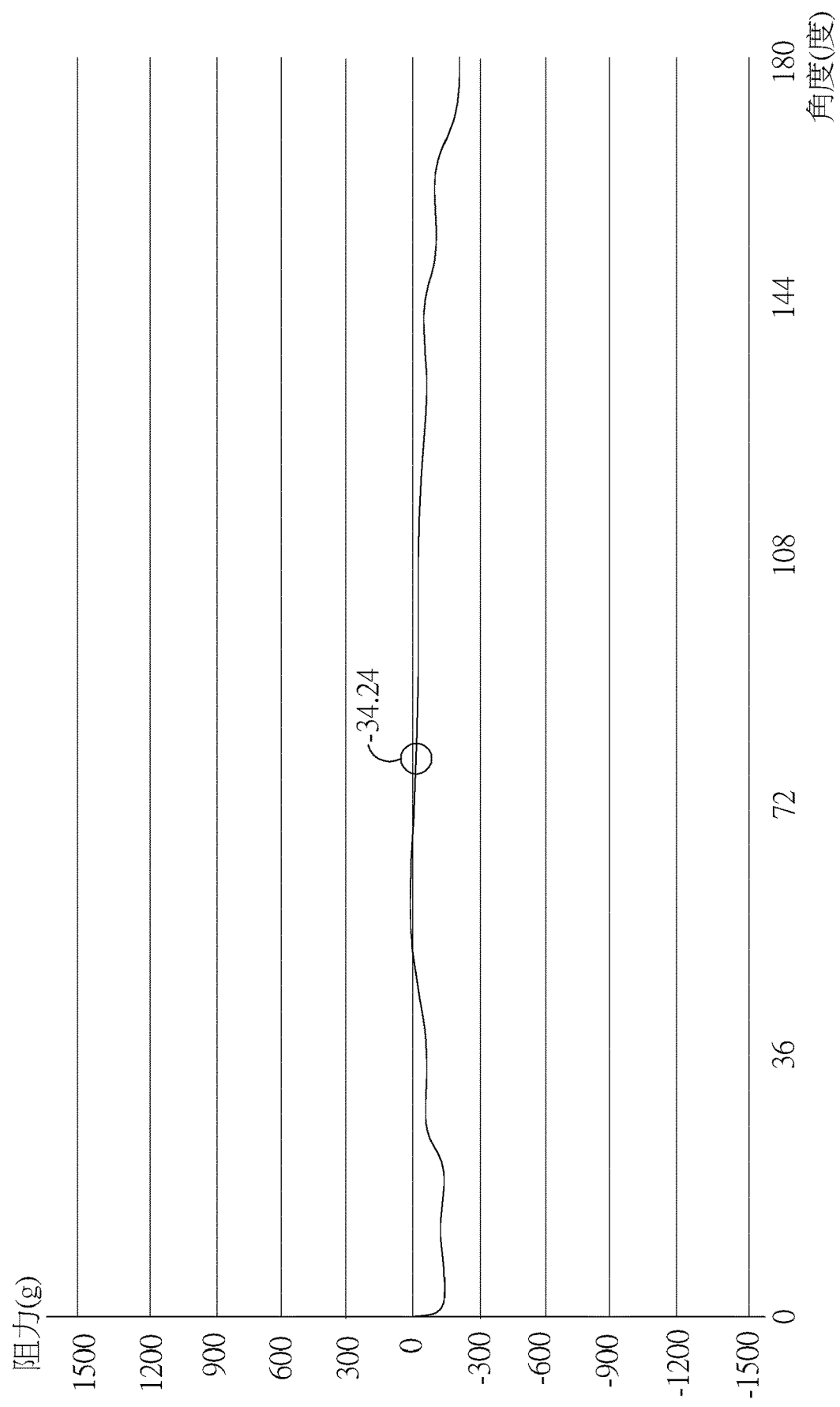
FIG. 7D is a curve of a first sensing signal and a second sensing signal during swinging of a contact module in a first axial direction of an embodiment according to the present invention.

360 and the second communication control circuit 406 provides a corresponding compensation according to the signal curve shown in FIG. 7D to avoid improper force applied by the contact module 10.

As shown in FIG. 7A-7D, the average value of the first reaction force F1 and the second reaction force F2 and the values of the third reaction force F3 and the fourth reaction force F4 are displayed in a real-time manner. For example, 140.50 g, −22.17 g, 221.81 g and −34.24 g are shown in FIG. 7A-7D. The grip control device 400 can be externally connected with a display unit (not shown in the figure) for showing the above values. The values and the signal curves of the present invention are not limited. They are determined according to materials for the contact module 10, output power and rotation angle of the first drive module 310, the second drive module 312, the third drive module 314, and the fourth drive module 316. At the same time, a value of the x-axis corresponding to a circle of the respective values in the figure is the rotation angle of the contact module 10 now.

In addition, refer to FIG. 3 and FIG. 7A-7D, at least one of the first communication control circuit 360 and the second communication control circuit 406 can be connected with an external input device (not shown in figure). In this embodiment, the second communication control circuit 406 is connected with a switch 450 and used for setting a mechanical load of the contact module 10 or an upper limit of a load of the contact module 10 while being applied with a force during the operation such as 3000 g. At least one of the first communication control circuit 360 and the second communication control circuit 406 is set with the upper limit of the load. When at least one of the first communication control circuit 360 and the second communication control circuit 406 is over the upper limit of the load, the first communication control circuit 360, the second communication control circuit 406, or both stop working temporarily. A surgeon performing surgery needs to turn on the switch 450 for generating and sending an activation signal to the second communication control circuit 406. Thus the first communication control circuit 360 and the second communication control circuit 406 are driven to work again. This is to remind the surgeon that the force applied has been over the upper limit of the load in order to avoid human errors associated with the operation.

In summary, the present surgical robot uses a plurality of the force sensing members disposed on the first robotic arm to detect the first reaction force and the second reaction force sent back by the contact module and generate a corresponding sensing signal sent to the first communication control circuit. Then the sensing signal is transferred to the second communication control circuit and a corresponding feedback control signal is produced. Thereby the grip driving member generates the force feedback corresponding to the feedback control signal for allowing the grip portion to move. Therefore, the surgical robot operator will not apply too much force to the control module during operation of the surgical robot and further surgical risk caused by the excessive force applied can be avoided.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A surgical robot comprising:
    at least one contact module:
    a control connection module provided with a first main body and a rod having a first end inserted through the first main body; a first transmission member is mounted in the control connection module and used for driving a first end of a first transmission connecting member while a second end of the first transmission connecting member is inserted through the rod and connected with the contact module at a second end of the rod;
    at least one first robotic arm which includes:
        a first shaft member linked to the first transmission member;
        a first force sensing member linked to the first shaft member and used for detecting a first reaction force and generating a first sensing signal while the first reaction force is transferred from the contact module to the first force sensing member through the first transmission connecting member, the first transmission member, and the first shaft member; and
        a first communication control circuit electrically connected with the first force sensing member for receiving and sending the first sensing signal; and
    at least one grip control device which includes a grip driving member, a grip portion, and a second communication control circuit; the grip driving member is linked to the grip portion and electrically connected with the second communication control circuit; the second communication control circuit is connected with the first communication control circuit through a remote transmission interface and receiving the first sensing signal through the remote transmission interface to generate a corresponding feedback control signal for control of the grip driving member; thereby the grip driving member generates a force feedback for driving the grip portion to move.

2. The surgical robot as claimed in claim 1, wherein the contact module includes a first contact member and a second contact member which are respectively corresponding to the first reaction force and a second reaction force; the second end of the first transmission connecting member is inserted through the rod and connected with the first contact member at the second end of the rod; wherein the first reaction force is transferred from the first contact member to the first force sensing member through the first transmission connecting member, the first transmission member, and the first shaft member; wherein a second transmission member and a second transmission connecting member are mounted in the first main body; the second transmission member drives a first end of the second transmission connecting member to move while a second end of the transmission connecting member is inserted through the rod and connected with the second contact member at the second end of the rod; wherein the first robotic arm further includes:
    a second shaft member disposed adjacent to the first shaft member and linked to the second transmission member;
    a second force sensing member which is electrically connected with the first communication control circuit, linked to the second shaft member, and used for detecting the second reaction force and generating a second sensing signal; the second reaction force is transferred from the second contact member to the second force sensing member through the second transmission connecting member, the second transmission member, and the second shaft member;
wherein the first force sensing member and the second force sensing member respectively send the first sensing signal and the sensing signal to the first communication control circuit; then the first communication control circuit sends the first and the second sensing signals to the second communication control circuit through the remote transmission interface so that the second communication control circuit generates and sends a corresponding feedback control signal to the grip driving member for control of the grip driving member; thereby the grip driving member generates the force feedback for driving the grip portion to move.

3. The surgical robot as claimed in claim 2, wherein the control connection module includes:
the first main body having a cover body, a bottom plate, and a fixing base disposed on the bottom plate;
the rod having the first end pivotally arranged at the fixing base and inserted through the cover body, and the second end provided with the contact module;
the first transmission member disposed on the bottom plate and connected with the first shaft member;
the first transmission connecting member having one end wound around the first transmission member while the other end of the first transmission connecting member is inserted through the rod and wound around the first contact member; the first transmission member drives the first contact member to move through the first transmission connecting member so that the first contact member swings relative to the rod with a degree of freedom in a first axial direction;
the second transmission member arranged at the bottom plate, located adjacent to the first transmission member, and connected with the second shaft member;
the second transmission connecting member having one end wound around the second transmission member while the other end of the second transmission connecting member is inserted through the rod and wound around the second contact member; the second transmission member drives the second contact member to move through the second transmission connecting member so that the second contact member swings relative to the rod with the degree of freedom in the first axial direction;
a third transmission member disposed on the bottom plate;
a fourth transmission member disposed on the bottom plate and arranged adjacent to the third transmission member;
a third transmission connecting member having one end wound around the third transmission member while the other end of the third transmission connecting member is inserted through the rod and wound around the contact module; the third transmission member drives the contact module to move through the third transmission connecting member so that the contact module moves relative to the rod with a degree of freedom in a second axial direction; and
a fourth transmission connecting member having two ends wound around the fourth transmission member and the first end of the rod correspondingly; during rotation of the fourth transmission member, the rod is adjusted through the fourth transmission connecting member and thus rotated around a central axis of the rod.

4. The surgical robot as claimed in claim 3, wherein the control connection module further includes a first pulley and a second pulley respectively arranged between the first and the fourth transmission members and between the second and the third transmission members; the first pulley is used to help the first transmission connecting member enter the rod smoothly while the second pulley is used to help the second transmission connecting member and the third transmission connecting member enter the rod smoothly.

5. The surgical robot as claimed in claim 3, wherein the first robotic arm further incudes:
a first drive module which is disposed on one side of the first force sensing member and the first shaft member, electrically connected with the first communication control circuit, and linked to the first shaft member;
a second drive module which is arranged at one side of the second force sensing member and the second shaft member, electrically connected with the first communication control circuit, and linked to the second shaft member;
a third shaft member connected with and linked to the third transmission member;
a third force sensing member which is electrically connected with the first communication control circuit and linked to the third shaft member for detecting a third reaction force and generating a third sensing signal while the third reaction force is transferred from the contact module to the third force sensing member through the third transmission connecting member, the third transmission member, and the third shaft member;
a third drive module arranged adjacent to the second shaft member, electrically connected with the first communication control circuit, and used for driving the third shaft member;
a fourth shaft member connected with and linked to the fourth transmission member;
a fourth force sensing member which is electrically connected with the first communication control circuit and linked to the fourth shaft member for detecting a fourth reaction force and generating a fourth sensing signal while the fourth reaction force is transferred from the rod to the fourth force sensing member through the fourth transmission connecting member, the fourth transmission member, and the fourth shaft member; and
a fourth drive module arranged adjacent to the third drive module and the first shaft member, electrically connected with the first communication control circuit, and used for driving the fourth shaft member;
wherein the second communication control circuit generates and sends a drive control signal to the first communication control circuit so that the first communication control circuit generates and sends a drive signal to the first drive module, the second drive module, the third drive module, and the fourth drive module according to the drive control signal for control of the first drive module to drive the first shaft member, for control of the second drive module to drive the second shaft member, for control of the third drive module to drive the third shaft member, and for control of the fourth drive module to drive the fourth shaft member.

6. The surgical robot as claimed in claim 5, wherein the first robotic arm further incudes:
a fifth shaft member disposed on one side of the first robotic arm;
a fifth force sensing member arranged at one side of the fifth shaft member, connected with the first main body, and electrically connected with the first communication control circuit, and
a fifth drive module disposed on one side of the first robotic arm for driving the fifth force sensing member and the fifth shaft member to move;
wherein first communication control circuit generates and sends a drive signal to the fifth drive module for control of the fifth drive module to move the fifth force sensing member by pushing or pulling; thereby the first main body is driven to have a displacement; the fifth force sensing member detects deformation of the fifth force sensing member itself and then generates and sends a fifth sensing signal to the first communication control circuit; the first communication control circuit further sends the fifth sensing signal to the second communication control circuit.

7. The surgical robot as claimed in claim 6, wherein the first drive module, the second drive module, the third drive module, the fourth drive module, and the fifth drive module are either swing motor drivers or integrated motor drivers; wherein the first force sensing member, the second force sensing member, the third force sensing member, the fourth force sensing member, and the fifth force sensing member are load cells.

8. The surgical robot as claimed in claim 6, wherein the grip control device further includes:
- a plurality of cantilevers connected end-to-end and connected with the grip driving member;
- a plurality of cantilever drivers pivotally connected with connection areas of the cantilevers and linked to the cantilevers; and
- a control base connected to a rear end of the connected cantilevers and provided with the second communication control circuit which is electrically connected with the grip driving member and the cantilever drivers; the second communication control circuit connected with the first communication control circuit through the remote transmission interface; the second communication control circuit receives the first sensing signal, the second sensing signal, the third sensing signal, and the fourth sensing signal through the remote transmission interface and hence generates the feedback control signal correspondingly for control of the grip driving member and the cantilever drivers to generate the force feedback; thus both the grip portion and cantilevers are driven to move; and
- at least one displacement driving module disposed on one side of the control base, electrically connected with the second communication control circuit, and linked to the control base for control of displacement of the control base; the second communication control circuit controls the displacement driving module to make the control base move according to the fifth sensing signal.

9. The surgical robot as claimed in claim 1, wherein the grip control device further includes:
- a plurality of cantilevers connected in series and connected with the grip driving member;
- a plurality of cantilever drivers pivotally connected with connection areas of the cantilevers and linked to the cantilevers; and
- a control base connected to a rear end of the connected cantilevers and provided with the second communication control circuit which is electrically connected with the grip driving member and the cantilever drivers; the second communication control circuit connected with the first communication control circuit through the remote transmission interface; the second communication control circuit receives the first sensing signal through the remote transmission interface and hence generates the feedback control signal correspondingly for control of the grip driving member and the cantilever drivers to generate the force feedback; thus both the grip portion and cantilevers are driven to move.

10. The surgical robot as claimed in claim 1, wherein at least one of the first communication control circuit and the second communication control circuit is set with an upper limit of a load while the second communication control circuit is electrically connected with a switch; when the force feedback corresponding to the feedback control signal is over the upper limit of the load, at least one of the first communication control circuit and the second communication control circuit stops working temporarily; when the switch is turned on to generate and send an activation signal to the second communication control circuit, at least one of the first communication control circuit and the second communication control circuit is driven to work again.

* * * * *